US011521711B2

(12) United States Patent
Murthy

(10) Patent No.: US 11,521,711 B2
(45) Date of Patent: Dec. 6, 2022

(54) SYSTEM FOR HANDLING INFORMATION RELATING TO CHEMICAL SUBSTANCES

(71) Applicant: ATONARP INC., Tokyo (JP)

(72) Inventor: Prakash Sreedhar Murthy, Tokyo (JP)

(73) Assignee: ATONARP INC., Tokyo (JP)

( * ) Notice: Subject to any disclaimer, the term of this patent is extended or adjusted under 35 U.S.C. 154(b) by 1244 days.

(21) Appl. No.: 15/944,248

(22) Filed: Apr. 3, 2018

(65) Prior Publication Data

US 2018/0225426 A1  Aug. 9, 2018

Related U.S. Application Data

(63) Continuation of application No. 13/000,667, filed as application No. PCT/JP2009/002872 on Jun. 23, 2009, now abandoned.

(30) Foreign Application Priority Data

Jun. 23, 2008  (JP) ................................ 2008-163540

(51) Int. Cl.
    *G16C 20/20*    (2019.01)
    *G16C 20/90*    (2019.01)
    *G16C 20/70*    (2019.01)

(52) U.S. Cl.
    CPC ............ *G16C 20/20* (2019.02); *G16C 20/90* (2019.02); *G16C 20/70* (2019.02)

(58) Field of Classification Search
    None
    See application file for complete search history.

(56) References Cited

U.S. PATENT DOCUMENTS

| 6,450,008 | B1 | 9/2002 | Sunshine et al. |
| 7,227,136 | B2 | 6/2007 | Walte et al. |
| 8,265,110 | B2 | 9/2012 | Dantus et al. |
| 2002/0151992 | A1* | 10/2002 | Hoffberg ............... G06F 3/0481 700/83 |
| 2008/0270083 | A1 | 10/2008 | Lange et al. |
| 2009/0124867 | A1 | 5/2009 | Hirsh et al. |

FOREIGN PATENT DOCUMENTS

| CN | 1556412 A | 12/2004 |
| EP | 1 817 718 B1 | 6/2012 |
| JP | 63-269050 A | 11/1988 |
| JP | 07-055742 A | 3/1995 |
| JP | 7-151730 A | 6/1995 |
| JP | 9-127069 A | 5/1997 |
| JP | 2000-156647 A | 6/2000 |
| JP | 2002-524205 A | 8/2002 |
| JP | 2002-524206 A | 8/2002 |
| JP | 2004-164303 A | 6/2004 |
| JP | 2005-338057 A | 12/2005 |
| JP | 2006-519985 A | 8/2006 |
| JP | 2007-192628 A | 8/2007 |
| JP | 2008-505344 A | 2/2008 |
| JP | 2008-508693 T | 3/2008 |
| WO | WO 00/015268 A1 | 3/2000 |
| WO | WO 00/15269 A1 | 3/2000 |
| WO | WO 2004/013890 A2 | 2/2004 |
| WO | WO 2004/038602 A1 | 5/2004 |
| WO | WO 2006/013396 A2 | 2/2006 |
| WO | 2008/068847 A1 | 6/2008 |

OTHER PUBLICATIONS

Cai et al. IEEE Sensors Journal, 2 (3), p. 230-234, 2002.*
Mielke et al Anal. Chem. 2008, 80, 8171-8177.*
International Search Report and Written Opinion for corresponding International Application No. PCT/JP2009/002872, dated Aug. 11, 2009.
International Preliminary Report on Patentability (English Translation) from corresponding International Application No. PCT/JP2009/002872, dated Feb. 17, 2011.
Keller et al., "Transmission of Olfactory Information for Telemedicine", Interactive Technology and the New Paradigm for Healthcare, Jan. 19, 1995, Chapter 27, XP000672044; p. 168-172.
Extended European Search report issued in corresponding European Patent Application No. 09769897.1, dated Feb. 10, 2016 (8 pages).
Lagenhove et al, "Gas Chromatography/Mass Spectrometry Identification of Organic Volatiles Contributing to Rendering Odors", Environ. Sci, Techno. 1982, 16, p. 883-886.
Cai et al., "Identification of Odors using a Sensor Array with Kinetic Working Temperature and Fourier Spectrum Analysis", IEEE Sensors Journal, vol. 2, No. 3, p. 230-234, Jun. 2002.
Chinese Office Action (The Second Office Action) dated May 28, 2013, issued by the State Intellectual Property Office of People's Republic of China in corresponding Chinese Patent Application No. 200980132948.X, and an English Translation of the Office Action. (40 pages).
Indian Examination Report dated May 23, 2017, issued by the Intellectual Property of India in the corresponding Indian Patent Application No. 9368/DELNP/2010. (11 pages).
Decision to Grant issued by the Japanese Patent Office dated Mar. 27, 2014 in corresponding Japanese Application No. 2010-517761, and English language translation of Decision to Grant. (5 pages).
Notice of Reasons for Refusal issued in corresponding Japanese Patent Application No. 2017-247226, dated Jul. 18, 2019, with English Translation (7 pages).

* cited by examiner

*Primary Examiner* — Michael L Borin
(74) *Attorney, Agent, or Firm* — Buchanan Ingersoll & Rooney PC

(57) ABSTRACT

A system for generating first data including content data includes an interface for outputting the content data, a conversion unit to convert an intensity change indicative of a detected chemical substance contained in data from a sensor into the content data. The sensor includes a mass spectrometric type sensor capable of controlling sensitivity, resolution or selectivity, and a hardware unit that is configured to carry out an analysis of the data with initial setting conditions designed for scanning in a first range using a test sample prepared in advance, change the setting conditions for the sensor for use with the conversion unit, based on the analysis carried out automatically and periodically, the setting conditions including at least one of a voltage for ionizing and a voltage for scanning a spectrum region for detecting a chemical substance requested by an application.

4 Claims, 17 Drawing Sheets

Fig. 5

| Chemical class | FG | Name | Formula | Sub-band | Sub-band frequency allocation (f0 – fm-1) | Frequency band |
|---|---|---|---|---|---|---|
| Organic | Alkanes | Ethane | C2H6 | SB-1 | SB-1,f0 | 50 – 1KHz |
| | | Methane | CH4 | | SB-1,f1 | |
| | | Propane | C3H8 | | SB-1,f2 | |
| | | Butane | C4H10 | | SB-1,f3 | |
| | | Pentane | C5H12 | | SB-1,f4 | |
| | | Hexane | C6H14 | | SB-1,f5 | |
| | | Heptane | C7H16 | | SB-1,f6 | |
| | | Octane | C8H18 | | SB-1,f7 | |
| | | Nonane | C9H20 | | SB-1,f8 | |
| | | Decane | C10H22 | | SB-1,f9 | |
| | | Undecane | C11H24 | | SB-1,f10 | |
| | | Dodecane | C12H26 | | SB-1,f11 | |
| | | Triacontane | C30H62 | | SB-1,f12 | |
| | Aldehydes | Formaldehyde | HCHO | SB-2 | SB-2,f0 | 1050 – 2Khz |
| | | Acetaldehyde | CH3CHO | | SB-2,f1 | |
| | | | | SB-3 | SB-3 f0-fm-1 | 2050 – 3Khz |
| | | | | SB-45 | SB-45 f0-fm-1 | 45.05 – 46Khz |
| | Disulfides | | | SB-46 | SB-46 f0-fm-1 | 46.05 – 47Khz |
| Inorganic | Carbon | Carbon monoxide | CO2 | SB-47 | SB-47 f0-fm-1 | 47.05 – 60Khz |
| | Nitrogen | Ammonia | NH3 | | | |
| | | Nitrogen dioxide | NO2 | | | |
| Unclassified | Unclassified | Comp -1 | | SB-48 | SB48-r0 | 61.05 – 70Khz |
| | | Comp - m-1 | | | SB48-r1 | |

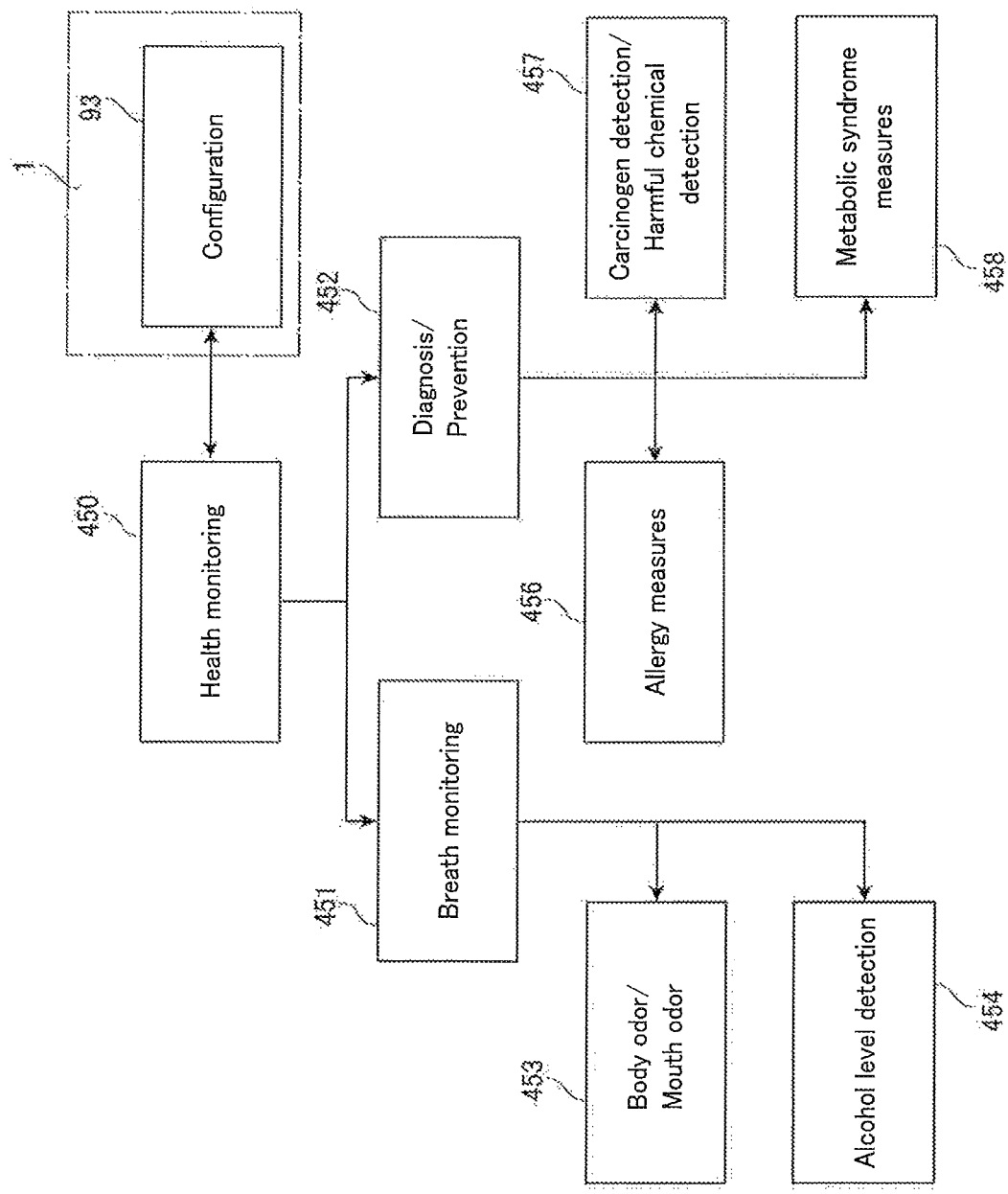

SYSTEM FOR HANDLING INFORMATION RELATING TO CHEMICAL SUBSTANCES

CROSS-REFERENCE TO RELATED APPLICATIONS

The present invention is a continuation of U.S. patent application Ser. No. 13/000,667, which was filed on Mar. 24, 2011, which is a national stage application of PCT/JP2009/002872, filed Jun. 23, 2009, which claims priority of JP 2008-163540, filed Jun. 23, 2008. The contents of U.S. patent application Ser. No. 13/000,667; PCT/JP2009/002872; and JP 2008-163540 are incorporated herein by reference.

TECHNICAL FIELD

The present invention relates to a system and method for handling constituents detected in air and the like.

BACKGROUND ART

A compact mass spectrometry apparatus that is based on micromachine technology has been disclosed (see PCT publications WO2006/013396 (published in translation in Japan as Japanese Laid-Open Patent Publication No. 2008-508693) and WO2004/013890). A system including an odorant fingerprint generator that provides an odorant fingerprint representing an arbitrary odor and an odorant concentration vector generator that receives the odorant fingerprint and generates an odorant concentration vector is disclosed in PCT publication WO00/15269 (published in translation in Japan as Japanese Laid-Open Patent Publication No. 2002-524206).

DISCLOSURE OF THE INVENTION

However, a system and method that transmits dynamic information relating to odors (smells, scents) in the same way as sound, images, and the like, processing such information together with data on sounds, images, and the like, and handling odors as information that forms part of multimedia has not been provided.

One aspect of the present invention is a system including an apparatus (generator) that generates first data including content data relating to chemical substances. Here, the chemical substances include at least one of compounds, molecules, and elements. The generator that generates (i.e., the apparatus that generates the first data) includes a conversion unit that converts intensity variations, which show detected chemical substances included in data from at least one sensor that detects an amount (physical amount) that changes due to presence of at least one of the chemical substances, to the content data by mapping onto a frequency space where a plurality of frequencies have been respectively assigned to a plurality of specified chemical substances. In the present specification, the expression "chemical substances" includes compounds, molecules, and elements, and also includes products without being limited to constituents and compositions.

Another aspect of the present invention is a system including: an interface that receives first data including content data where intensity variations showing chemical substances have been mapped onto a frequency space where a plurality of frequencies have been respectively assigned to specified chemical substances; and a reproduction apparatus that supplies odor data based on the content data of the first data to a device driver, wherein the device driver includes a function that converts the odor data to a combination of a plurality of odor sources that are used in an odor generating apparatus.

Yet another aspect of the present invention is a method of generating first data including content data relating to chemical substances. The method includes converting intensity variations, which show chemical substances, to the content data by mapping onto a frequency space where a plurality of frequencies have been respectively assigned to a plurality of specified chemical substances.

Yet another aspect of the present invention is a method of generating odors, including: receiving first data including content data produced by mapping intensity variations showing chemical substances onto a frequency space where a plurality of frequencies have been respectively assigned to a plurality of specified chemical substances; and converting, by a device driver, the odor data to a combination of a plurality of odor sources that are used in an odor generating apparatus.

Yet another aspect of the present invention is a program for causing a computer to function as an apparatus that generates first data including content data relating to chemical substances. The program (program product) can be provided having been recorded on an appropriate recording medium such as a CD-ROM. The program (program product) can also be provided via a computer network such as the Internet.

BRIEF DESCRIPTION OF THE DRAWINGS

FIG. 5 is a diagram showing a lookup table.
FIG. 19 is a flowchart showing applications for health monitoring.

DETAIL DESCRIPTION OF THE PRESENT INVENTION

Figure 1:
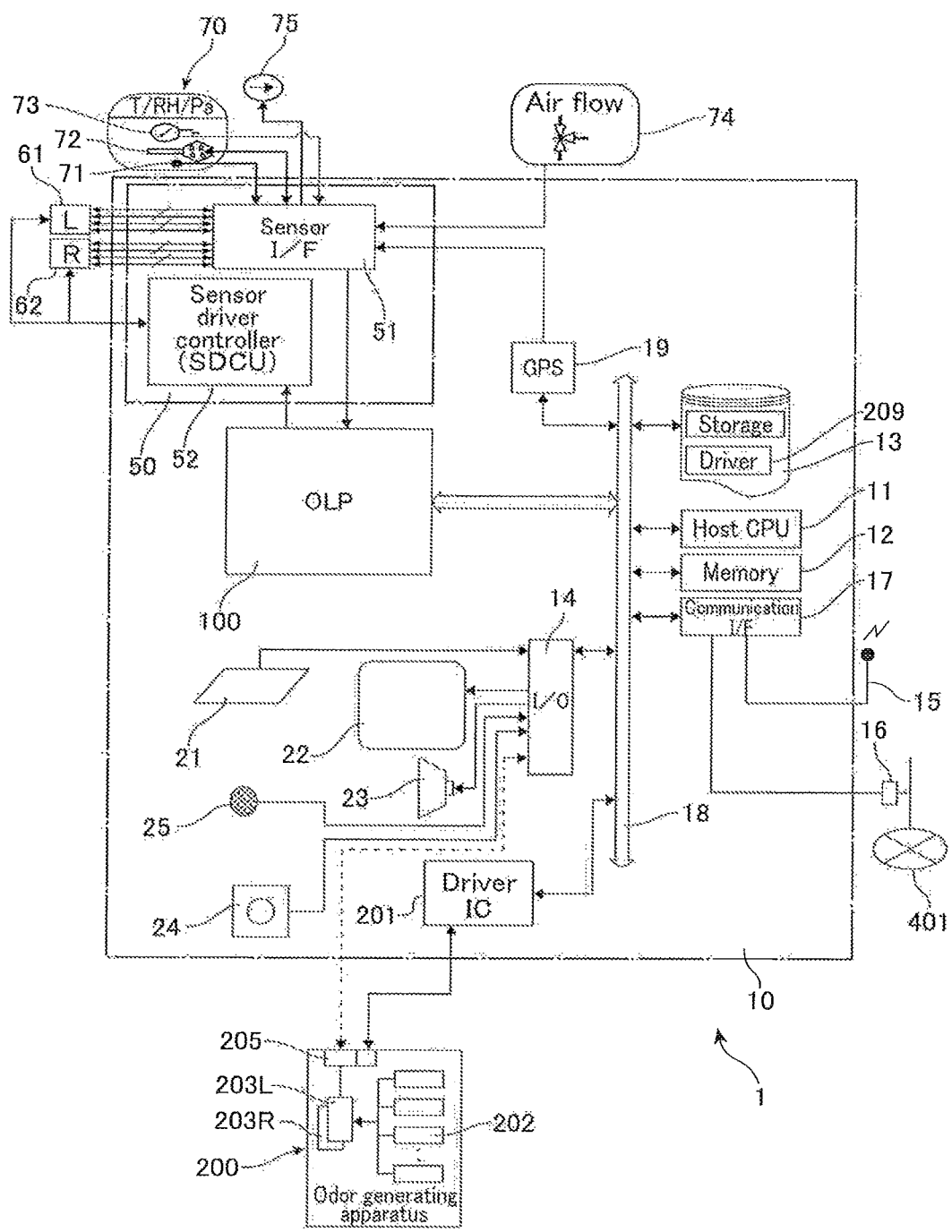
FIG. 1 is a block diagram of a system.

FIG. 1 shows one example of a system according to the present invention. This system 1 is typically realized as a system 1 that is centered on a notebook-type personal computer 10. The personal computer (PC) 10 includes a CPU 11, a suitable memory 12, storage 13 such as a hard disk drive, a local input/output interface 14 that provides a user interface, a communication interface (transceiver) 17 for exchanging data with an external appliance via a wireless connection 15 or a computer network 16, and a bus system 18 that connects such components. An input appliance such as a keyboard 21, an image output appliance such as a liquid crystal display 22, an audio output appliance such as a speaker 23, an appliance that obtains audio information such as a microphone 25, and an appliance that obtains image information such as a camera 24 are connected to the local input/output interface 14. The system 1 may include such input/output devices or may be provided with interfaces for connecting such input/output devices.

A device (GPS) 19 that carries out positioning using electromagnetic waves from a satellite, a device that provides an olfactory function (olfaction processor, OLP) 100, and a driver device (driver IC) 201 for driving an odor generating (reproduction) apparatus 200 are also connected to the bus 18. The OLP 100 is capable of being provided as a single integrated device (chip) or as a plurality of integrated chips (chipset). If the odor generating apparatus 200 is provided with a function for connecting via a universal deployment (general-purpose) interface such as USB, the odor generating apparatus 200 can be connected as shown by the broken line to the local input/output interface 14 instead of being connected to the dedicated device 201. The odor generating apparatus 200 typically includes a plurality of odor sources (odor generators) 202, left and right mixers 203L and 203R that generate desired odors by mixing such odor sources, and a control unit 205.

The PC 10 further includes a sensor controller device 50. The sensor controller device 50 is controlled by the OLP 100 and functions so as to provide various data to the OLP 100. The sensor controller device 50 includes a sensor interface 51 that is connected to various types of sensor and obtains (samples) data, and a sensor driver controller unit (SDCU) 52 that is capable of changing the measurement conditions of a number of sensors. Typical sensors are left and right mass spectrometer units (MSU) 61 and 62 that function as left and right nostrils. The measurement conditions of the MSUs 61 and 62 are controlled by the SDCU 52.

One example of the MSU 61 and 62 is an ion mobility mass spectrometry apparatus disclosed in PCT publication WO2006/013396 or PCT publication WO2004/013890). Such apparatuses are monolithic or micromachine-type compact mass spectrometry apparatuses, and are sufficiently portable. A plurality of sensor groups (environmental information sensor groups) 70 for measuring environmental information (environmental conditions) such as temperature and humidity are also connected to the sensor interface 51. The sensor groups 70 for measuring environmental conditions include a temperature sensor 71, a humidity sensor 72, a pressure sensor 73, and an air flow sensor 74. Positioning data produced by the GPS 19 can also be used as a position sensor input. In addition, the sensor interface 51 includes a function for controlling an air pump 75. However, this air pump 75 is not an essential component. According to requests from an application, outside conditions, and the like, the air pump 75 is capable of forcibly supplying outside air to the sensor group 70 described above for measuring environmental information and/or MSU 61 and 62 that are olfactory sensors.

The smallest unit in a system that includes the OLP 100 is the device 100 (an integrated circuit chip) itself. A system that includes the OLP 100 may be the PC 10, the system 1 that includes the odor generating apparatus 200, or may be an air conditioning system, a vehicle, an aircraft, manufacturing equipment, a building, medical equipment or the like that is equipped with the OLP 100.

The OLP 100 is a device or apparatus that is equipped with an olfactory function and is capable of converting odors (smells, scents, aromas) in outside air or peripheral air to data (stream data or a data stream) in real time. In addition, the OLP 100 is capable of encoding and decoding such data. Information on odors has the potential to play an important role in a large number of applications relating to virtual reality, multimedia, health, and safety. The OLP 100 can provide a portable household apparatus or PC with an olfactory function and make it possible to process data on odors via signal processing technology for audio and images.

Odors are caused by chemical substances such as chemical compounds, constituents and gases that are included in ambient air. In the following, the expression "chemical substances" includes chemical compounds, molecules, and elements and also includes products without being limited to constituents and compositions. Such causes of odors can be detected by sensors such as a crystal sensor (a quartz crystal microbalance or QCM), an electro-chemical sensor, a SAW (surface acoustic wave) device, an optical sensor, gas chromatography, and a mass spectrometry apparatus. Such sensors, are capable of detecting amounts (physical quantities) that change (fluctuate) due to the presence of chemical substances. Many of such sensors are bulky and complex, and are not easy to utilize in applications in habitual use. In addition, a number of such sensors have limitations in that they are sensitive for only a small number of gases or other specified chemical substances or have a sensitivity that changes in accordance with temperature and humidity.

In recent years, analyzing apparatuses that are capable of detecting the causes of odors and are compact and capable of being carried as described above have been studied. An analyzing device that uses ion mobility or optics (infra red, NMR) is capable of providing a small form factor sensor in the form of a single chip and has the potential of being used in a variety of applications including health and safety management in the home.

A mass spectrometry apparatus has wider applicability than a sensor that is sensitive to specified constituents (chemical substances) and detects the presence and intensity (concentration) of almost all constituents within the analyzed range with substantially the same precision. However, a mass spectrometry apparatus outputs a large amount of data that suggests the presence of chemical substances. This means that when data of a mass spectrometry apparatus is processed by the CPU 11 of the PC 10, the processing performance of the CPU 11 is occupied. Unless the processing performance of the CPU 11 is extremely large, there is the risk that it will not be possible to execute other applications for realizing an olfaction and/or that the processing performance will be significantly limited. The OLP 100 is designed to also provide a solution to such problem. That is, by providing the OLP 100 as a single chip in a household appliance such as a television set, an extremely handy electronic terminal such as a mobile telephone, a home security appliance, or the like and not just in the system 1 that is based on the PC 10 as shown in FIG. 1, it is possible to economically equip devices with an olfactory function.

By using a MEMS sensor such as a field asymmetric mass analyzer (Field Asymmetric waveform Ion Mobility Spectrometry (FAIMS) or Differential Ion Mobility Spectrometry (DIMS)) together with the OLP 100, it is possible to provide the system 1 that is capable of recording, generating, and recognizing odors at a low cost without requiring a high-cost CPU or DSP, without requiring large mechanical parts, and without requiring complex control circuitry.

The system 1 that uses the OLP 100 has extremely wide applicability and expandability, and can be used for a great variety of purposes. First, the OLP 100 is capable of providing a common or standard data format not only for input data from a spectroscopic sensor but also for input data from a variety of sensors (i.e., sensors capable of detecting chemical constituents) that includes IEEE 1451-compliant chemical, QCM, electrochemical, SAW, and MOS (Metal Oxide Semiconductor) sensors. In addition, the OLP 100 is capable of supporting the standard interfaces and data formats defined by MPEG (Moving Picture Experts Group), RoSE (Representative of Sensory Effect) and NOSE N/W (Second Network on Artificial Olfactory Sensing (Nose II)). Accordingly, it is possible to suppress the cost of making the system 1 compliant with a variety of sensors. The user is also capable of inputting and outputting odor information using data that conforms to a variety of standards. This means that it is possible to improve the usage efficiency of the system 1 and to provide a system with wide applicability at effectively low cost.

The OLP 100 is also capable of converting (generating) information on chemical constituents (chemical substances) detected by sensors to dynamic data (or a data stream). By converting information on odors to a data stream, it is possible to include odors in multimedia together with sound and/or images. In addition, it is possible to transfer odors in real time via a communication medium or communication infrastructure such as a wireless connection or the Internet. Additionally, by making use of data processing such as compression, encryption, and expansion (decompression) that are already carried out on sound and image data, it is possible to compress, encrypt, and/or expand odor information.

By successively analyzing "one-shot" pieces of odor information that have been converted to a data stream, it is possible to recognize and monitor odors on the fly. In addition, since information on chemical substances is converted to a common data format, processing that determines and recognizes target substances can be carried out with higher speed and a lower processing load, and it is also possible to standardize pattern data that is subjected to pattern recognition. Accordingly, it becomes possible to provide a large number of patterns for determining a variety of substances with odors in an economic manner. Pattern recognition of odors by a machine involves equipping a portable apparatus or a computational apparatus with a machine olfactory function, and can be used in a variety of fields, such as discovering threats to security, diagnostic routines during medicine, health monitoring of individuals, and the like. In addition, the odor data generated by the OLP 100 becomes wildly usable data input to various types of odor reproducing apparatus for real-time, dynamic, or static reproduction of odors.

Figure 2:
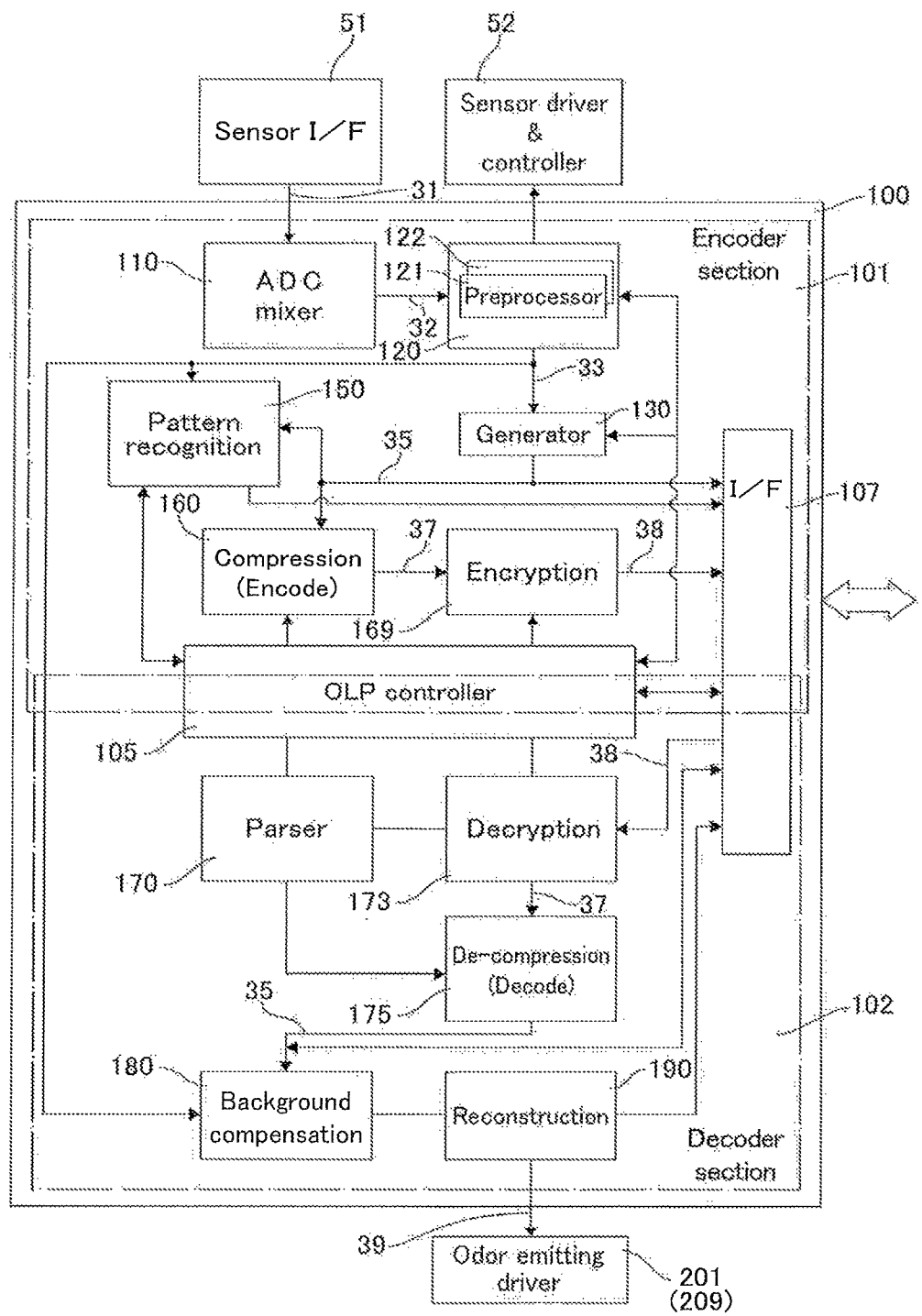
FIG. 2 is a block diagram of an OLP.

The OLP 100 will be described mainly in the order stated below.
1. Outline of OLP (FIG. 2)
2. Data Generation by OLP
2.1 Overview (FIG. 3)
2.2 Mapping Data of Chemical Substance Space (Chemical Substance Characteristic Space) onto Frequency Space
2.3 Mapping using Sub-band Images (FIGS. 4 to 6)
2.4 Generation and Output of Stream Data
2.5 Stereo Image
2.6 Inclusion of Supplementary Information aside from Chemical Substance Information
2.6.1 Environmental Information (Temperature, Humidity, Pressure)
2.6.2 Air Flow
2.6.3 Time
2.6.4 Position
2.7 Preprocessor (Reconfiguration of Measurement Conditions) (FIGS. 7, 8)
2.8 Accommodating Multiple Sensors
3. Substance Recognition by OLP (FIG. 9)
4. Data Compression by OLP (FIG. 10)
5. Data Reproduction and Output by OLP
6. Various Supplementary Information about OLP
7. Applications
1. Outline of OLP (FIG. 2)

The OLP 100 includes a section 101 that generates and encodes data, a section 102 that receives and decodes data, and an OLP controller 105 that controls the entire OLP 100. The OLP 100 may alternatively include one of the encoder section 101 and the decoder section 102. The OLP 100 is provided as a single device (integrated circuit or chip), but is also capable of being provided as a chipset, and is capable of being provided as a program (program product) that can be executed by a CPU or MPU equipped with suitable performance.

The encoder section 101 includes an ADC unit (ADC Mixer) 110 that receives (inputs) data 31 from a sensor interface 51, a preprocessor section 120 that carries out preprocessing, a generator 130 that carries out data generation, a recognition section 150 that carries out pattern recognition on data, a compression/encode unit 160 that compresses data, and an encryption unit 169 that encrypts the compressed data. The data inputted from the sensor interface 51 may be analog data or may be digital data. Analog data 31 is digitized by the ADC unit 110 and is sent as digital data 32 to the preprocessor section 120 that carries out preprocessing. The preprocessor section 120 includes a plurality of types of preprocessors 121 and 122 that differ according to sensor type or the like.

The generator 130 generates first data (variously indicated as "data stream", "RAW data", "raw data before processing such as compression") 35 that includes content data (container data) $139d$ (left and right information $139d$L and $139d$R) that relates to chemical substances. In the example below, the content data $139d$ includes left and right information $139d$L and $139d$R, but when the descriptions are common to the left and the right, L and R that indicate left and right are sometimes omitted. The content data $139d$ is stream data (stream-type data which like an audio data that has little temporal locality) produced (generated) by mapping variations in intensity (which include variations in concentration, variations in presence, and other changes—variations detected by sensors) of constituents or chemical substances (which here includes at least one of compounds, molecules, and elements) detected according to data 32 inputted from sensors via the sensor interface 51 onto a frequency space. To enable the intensity variations that show chemical substances to be mapped onto a frequency space, the plurality of frequencies in the frequency space are respectively assigned in advance to a plurality of specified chemical substances according to appropriate rules.

RAW data 35 may be data on a frequency region (frequency space) or may be data produced by converting (via inverse FFT) such data to a time region (time space). A typical example of the RAW data 35 is PCM (Pulse Code Modulation) type data. The RAW data 35 may also be QMF (Quadrature Mirror Filter) type data that has been divided into sub-bands by a QMF or the like. Such RAW data 35 may be outputted as it is from the interface 107 of the OLP.

In the recognition section 150, stream-type RAW data 35 is converted to temporally local data, and the substances included in the RAW data 35 are determined. The compression/encode unit 160 and the encryption unit 169 compress and encrypt the RAW data 35 according to an appropriate reversible or irreversible method. The RAW data 35 is fundamentally produced by converting all of the information inputted from a sensor to a frequency space. During compression, it is possible to improve the compression ratio by deleting parts that include information that is not required by an application and/or parts with a low information density.

The decoder section 102 includes a decryption unit 173 that receives and decrypts encrypted data, a reproduction analyzing unit (parser) 170 that analyzes the decrypted data, and a de-compression (decompression/decode) unit 175 that carries out de-compression (expansion) according to an appropriate method based on the results of the parser 170 to restore the RAW data 35. The decoder section 102 also includes a correction (background compensation) unit 180, which receives information (scan data) 33 relating to the real time environment and chemical substances in the periphery of the system from the preprocessor section 120 and compensates the RAW data 35, and a reconstruction unit 190 that reconstructs or reforms the compensated RAW data 35 in accordance with the sensitivity of the human sense of smell or the like and outputs the result as odor data 39. In this specification, the expression "odor" includes all information that can be sensed by the sense of smell, such as odors, smells, scents and aromas. Note that in the following description, the expression "odor" is used.

The odor data 39 is outputted from the OLP interface 107 and is supplied to the driver 201 of the odor generating (reproducing) apparatus (odor emitter) 200 via the bus 18 of the system 1. The driver 201 may be provided as a dedicated circuit or may be provided as a program 209 that is executed by the CPU 11 of the system 1. In the driver 201 or the driver 209 loaded by a program, the odor data 39 is converted into a combination of odor sources 202 that can be used in the odor reproducing apparatus 200. The odor data 39 is PCM-compatible data and includes intensity variation data that shows (suggests) the presence of individual chemical substances that have been mapped onto a frequency space. Accordingly, the odor data 39 is stream-type data in which information on a plurality of chemical substances is included in a universal format (universal deployment format) or a standardized format. This means that the manufacturer who provides the odor generating apparatus 200 is capable of providing a universal driver 201 or 209.

2. Data Generation by the OLP
2.1 Overview (FIG. 3)

Figure 3:
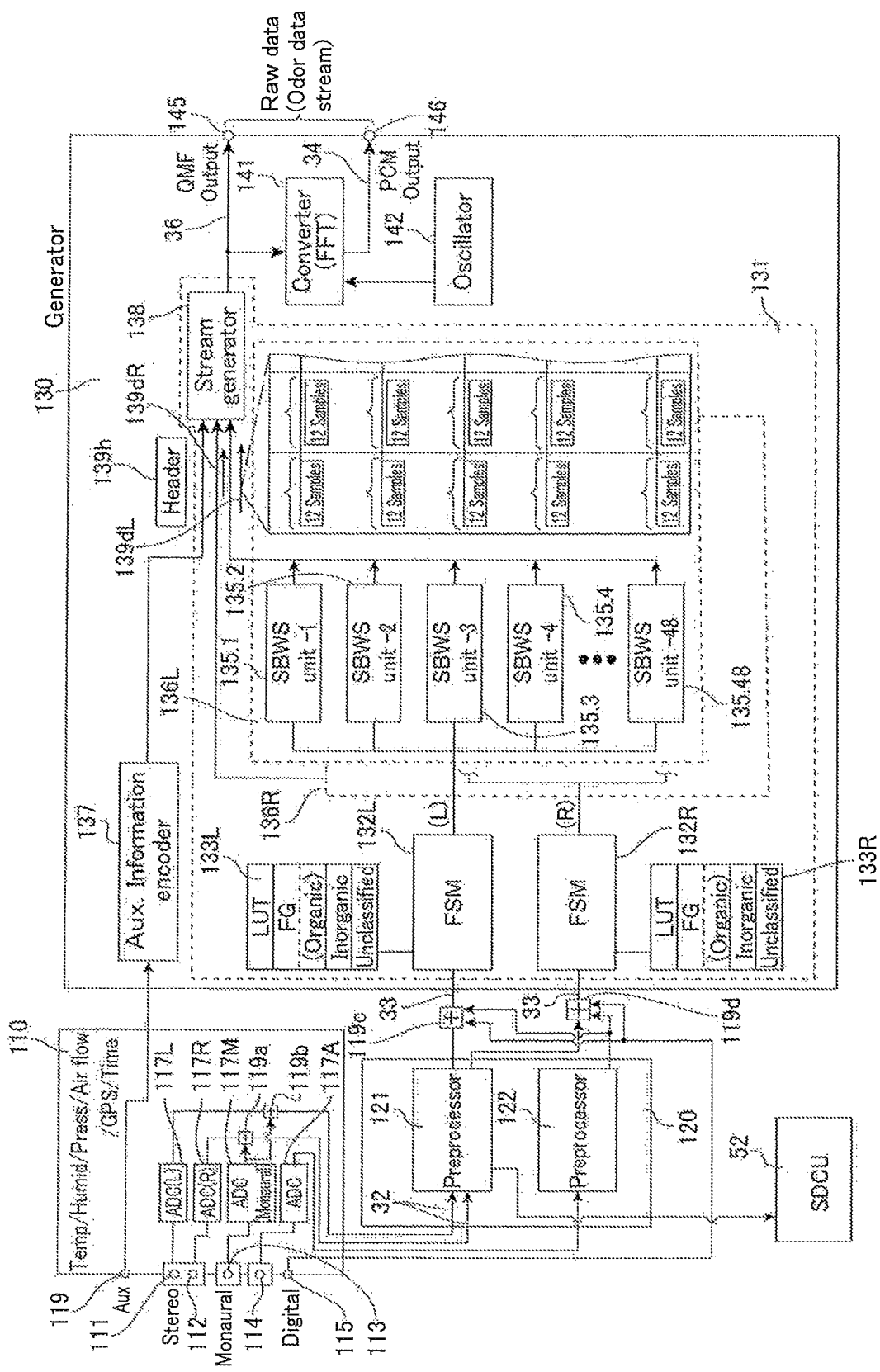
FIG. 3 is a block diagram of a periphery of a generator.
Figure 11:
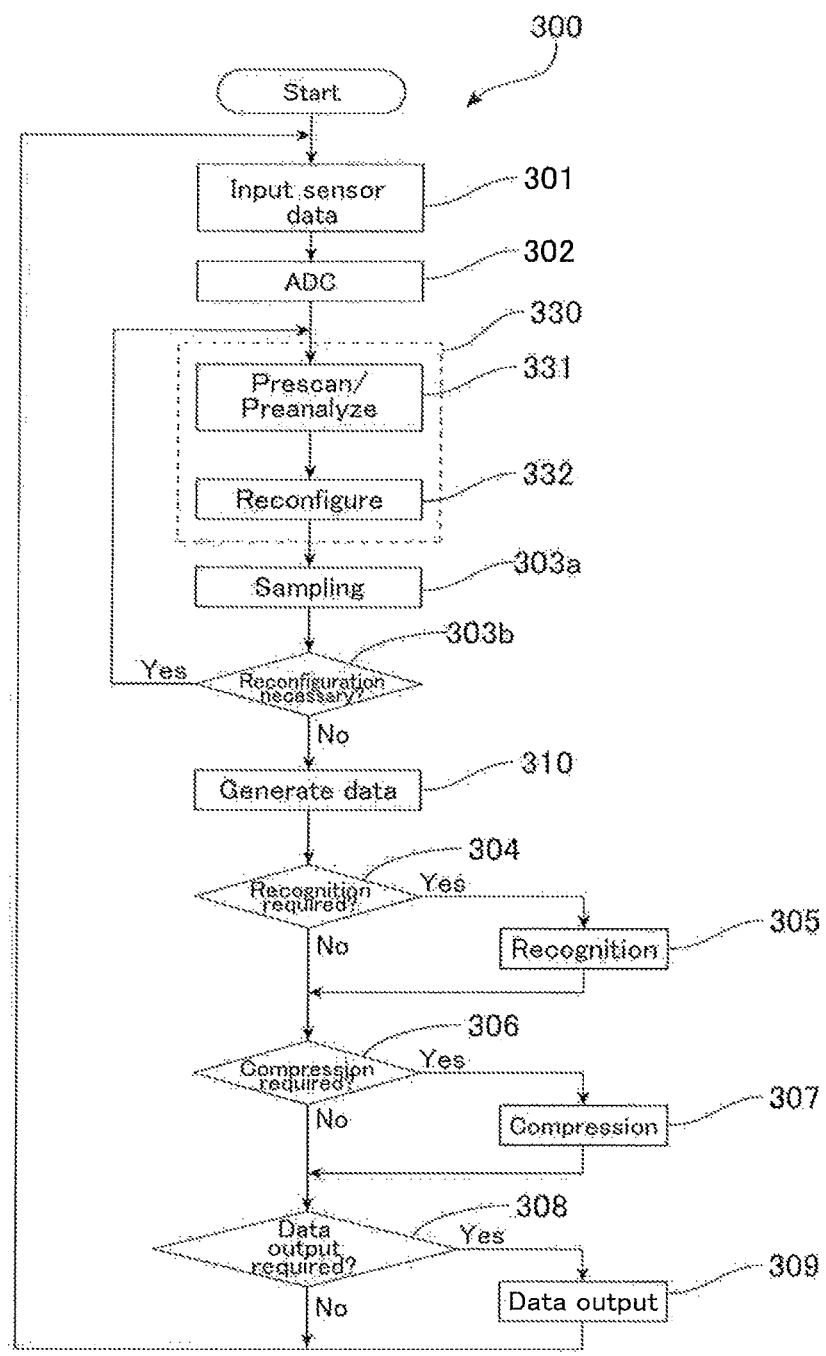
FIG. 11 is a flowchart showing a process that generates RAW data.

FIG. 3 shows a part that generates the RAW data ("RAW data stream" or "first data") 35 extracted out of the plurality of functional units included in the OLP 100. Also, FIG. 11 is a flowchart showing an overview of the process (generation method) that generates the RAW data 35 in the encode section 101 of the OLP 100.

The system 1 equipped with the OLP 100 includes a function that generates the RAW data (first data) 35 that includes the content data 139*d*. In the example below, the generating function is provided by the device referred to as the OLP 100 but the generating function may be provided by a program. The generator 130 that generates the RAW data 35 includes a conversion unit 131 that converts the intensity variations that show (suggest) the detected chemical substances included in the data obtained directly or indirectly from at least one sensor to the content data 139*d* by mapping onto a frequency space in which a plurality of frequencies have been assigned in advance to a plurality of specified chemical substances.

As stated earlier, the expression "chemical substances" includes compounds, molecules, and elements and also includes products without being limited to constituents and compositions. The expression "intensity variations" includes changes in the presence/absence and intensity (concentration) of chemical substances and constituents, that is, concentration variations and presence/absence (variations in presence), and may includes variations in a state relating to the presence of a substance detected by a sensor.

The method 300 that generates the first data (RAW data) 35 including the content data 139*d* includes converting (step 310) the intensity variations showing the chemical substances (which includes at least one of compounds, molecules, and elements) detected using data from at least one sensor to the content data 139*d* by mapping onto a frequency space in which a plurality of frequencies have been assigned to a plurality of chemical substances. The chemical substances detected according to the data from the sensor, that is, the chemical substances as detected, may be substances that are ultimately determined according to the data from the sensor, but may also be fragment constituents in mass spectrometry. Also, constituents where M/Z (mass per unit electrical charge) is the same may be represented by a chemical substance that is provisionally assigned according to appropriate or specified rules.

The generated RAW data 35 includes the content data 139*d* in which the intensity variations, which show chemical substances including at least one of compounds, molecules, and elements, have been mapped onto a frequency space in which a plurality of frequencies have been respectively assigned to a plurality of chemical substances, and can be provided having been recorded on an appropriate recording medium such as a memory, a CD-ROM, or a hard-disk drive. The RAW data 35 does not necessarily need to include information on chemical constituents or chemical substances that are ultimately analyzed. Conversely, out of the data from the sensors, it is preferable to include information that may possibly be needed to identify chemical substances, even if such information is classified into chemical substances that differ to the actual substances.

It is also possible to broadcast or distribute the RAW data 35 on a transmission medium that may be wireless or wired. It is also possible to distribute the RAW data 35 via a computer network such as the Internet. Accordingly, using infrastructure, a system, and/or an apparatus that broadcasts, transmits and receives, or distributes other multimedia information such as audio and images, it is possible to broadcast, transmit and receive, or distribute the RAW data 35 which includes the content data 139*d*, or information produced by compressing the RAW data 35, in the same way as other multimedia information.

2.2 Mapping Data of Chemical Substance Space (Chemical Substance Characteristic Space) onto Frequency Space (FIG. 3)

Analysis or parse of chemical constituents is carried out on a variety of targets having forms of solids, liquids, gases, or others existed in spaces. The invention included in this application is capable of converting constituents (chemical substances) detected in all of such forms to data or contents and using such data or contents in data processing, transmission, recording, reproduction or the like. Constituents present in the atmosphere are detected by the sense of smell out of the five senses. Accordingly, in the following explanation, an example is described where the present invention is used in an application where an olfactory function is provided in an information processing apparatus.

It is probably possible to detect compounds in the atmosphere with a sensor and then use a variety of signal processing and pattern matching techniques via electrical signals to specify the odors in the atmosphere. However, the compounds that are capable of being detected and the sensitivity for such compounds that are capable of being detected both change depending on the type of sensor and the characteristics of the sensor. Accordingly, it is preferable to provide a system that uses the same process to convert a variety of odors to data and reproduce the odors.

When generating information for transmitting or processing odors by specifying odors using a recognition technique such as pattern matching, the specified odors are static data, i.e., information that is temporally localized. Accordingly, it is preferable to provide a system for recording and reproducing odors that have little temporal locality and change dynamically.

Along with sight and hearing, smell is one of the five senses and detects changes that are continuous over time. Accordingly, to configure odors as multimedia together with music, voices, images, and the like, it is preferable to record and reproduce odors as stream-type data. Providing such a technology is one of the objects of the present embodiment.

Out of the constituents that can be present in the atmosphere, only a limited number of constituents can be detected by the sense of smell. Constituents that are not usually detected or noticed by the sense of smell have little value as odors. However, constituents that cannot be detected by the sense of smell (and in particular the human sense of smell) may indicate danger to human life. It is also effective to provide a technology that deletes information that has little value as odors or alternatively makes effective use of information that has little value as odors but is of high value in other applications.

The generator 130 of the OLP 100 maps (assigns) a space (chemical substance space) characterized by chemical substances onto a frequency space using FCWS (Functionally (i.e., Functional Group) Classification Wave Shaping) technology to convert intensity information showing the presence of chemical substances to intensity information for frequency regions. That is, the changes over time of the detected intensity variations of the respective chemical substances are converted to intensity variations of signals of frequencies that set so as to correspond to the respective chemical substances. By carrying out FCWS, signals showing odors are mapped onto a frequency space, redefined, and outputted as odor streams.

A great amount of processing of data showing intensity variations of signals of frequencies in the audible region has been developed as processing of audio data. A great amount of processing of data showing intensity variations of signals of frequencies in the visible region has been developed as processing of image data. Accordingly, by mapping data on chemical substances onto a frequency region, it becomes possible to use a lot of established techniques in signal processing. It also becomes possible to process odor data using the same platform as audio data and/or image data.

The conversion unit (FCWS unit) 131 of the generator 130 generates the RAW data 35 that has an interface and data format that are capable of being standardized. This means that there is extremely wide applicability. As an example, this technology is an effective means in encouraging a standardization organization such as MPEG or IEEE to standardize the data format and interface of odor data.

Figure 4:
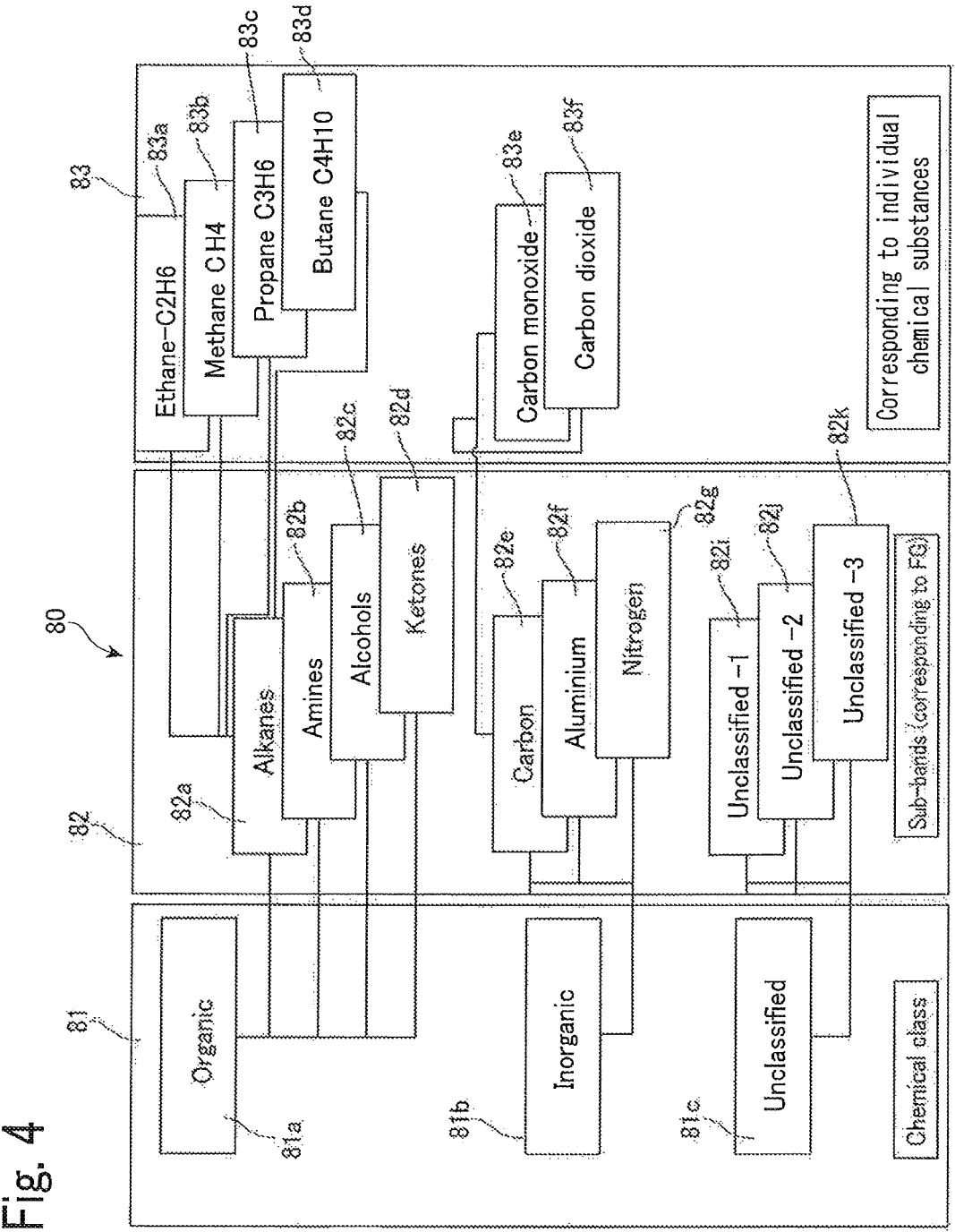
FIG. 4 is a diagram of grouping (corresponding to subbands).

2.3 Mapping Using Sub-Band (Multi-Band) Images (FIGS. 4 to 6)

With the FCWS technology illustrated here, a plurality of chemical substances are divided into a plurality of groups and a plurality of sub-bands are respectively assigned to the plurality of groups. If the number of chemical substances to be converted to data were low, there is the risk that the load of the data processing due to conversion to sub-bands (multi-bands) would be excessive. However, there is a huge number of types of chemical substances that are included or may be included in the atmosphere, so that conversion to sub-bands is effective for almost every type of data processing, such as pattern matching and compression.

Figure 12:
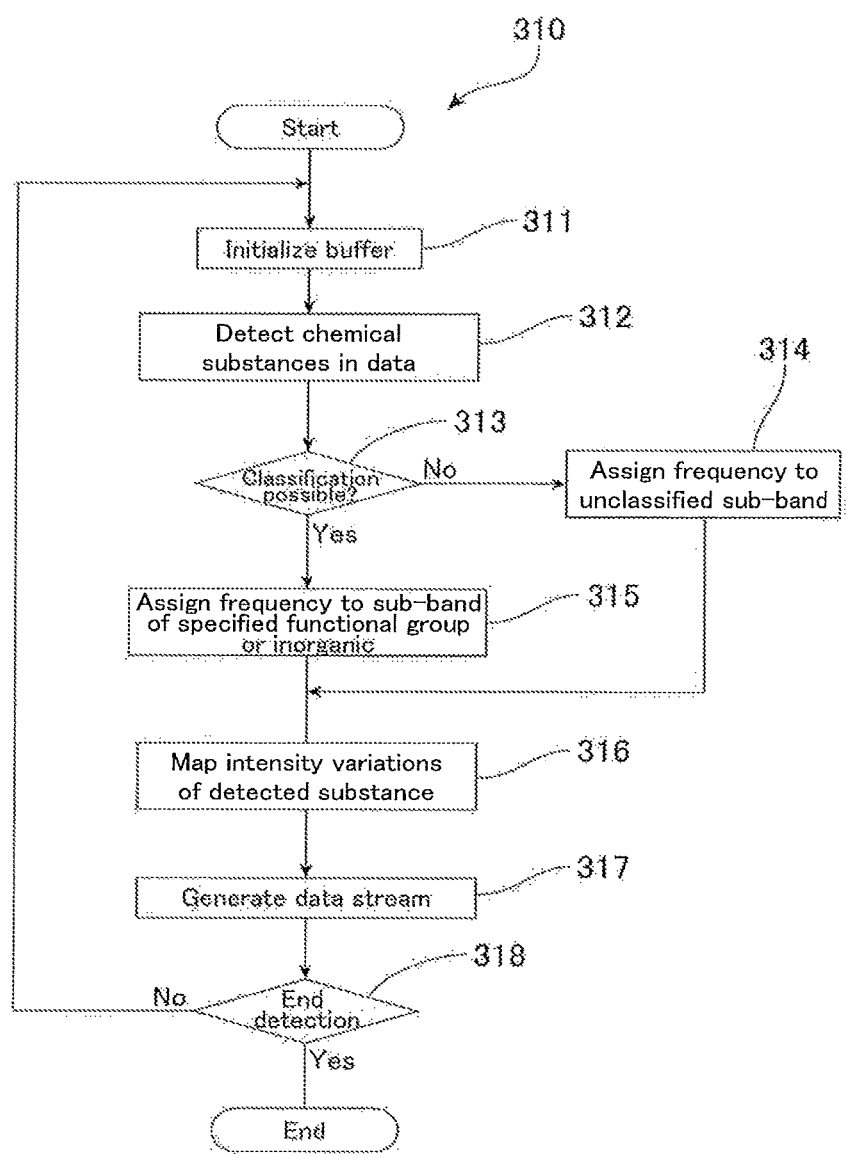
FIG. 12 is a flowchart showing a mapping process.

Accordingly, the conversion unit 131 converts the intensity variations showing the detected chemical substances to intensity variations of frequencies included in any of the sub-bands. Generation in the method 300 that generates data (i.e., the converting step) (step 310) includes conversion of intensity variations showing the detected chemical substances to intensity variations of frequencies included in any of the sub-bands. The detailed processing of sub-band waveform shaping is shown in FIG. 12.

When the conversion unit 131 processes the result of converting odors to data, that is, if the content data 139$d$ included in the RAW data (first data) 35 is odor data for transmitting information for analyzing odors and/or information relating to odors, a plurality of groups (referred to as functional groups, FG) should preferably include a plurality of groups that have been divided or determined according to functional groups of organic matter. In addition, the plurality of groups FG should preferably include inorganic matter groups and an unknown group.

The odor space that can be detected by the human sense of smell is closely related to functional groups in chemistry. Accordingly, mapping chemical substances detected according to data 33 inputted from a sensor onto a frequency space where functional groups in chemistry have been associated with the human odor space is effective for recording and reproduction. Odorant constituents exhibit different behavior depending on environmental variables such as humidity and temperature, with part of this depending on functional groups. For this reason also, it is effective to group chemical substances according to functional groups. In this example, a hierarchical group construction is proposed with chemical classes at the origin and further classification continuing on the next level based on chemical functional groups as the functional groups FG. As one example, 46 groups can be given as the functional groups, with the addition of the two groups "inorganic" and "unknown" ("non classifiable" or "unclassified") forming a total of 48 groups. It is possible to assign suitable frequency bands (sub-bands) to these groups and to sort (separate) groups of chemical substances that have the respective functional groups into frequency regions. It is also possible for the user to add sub-bands and/or classification categories based on system requirements.

A typical example of the sensors 61 and 62 for detecting chemical substances is a chip-based mass spectrometer (MS) that uses MEMS. In each sampling time (scan), the sensors 61 and 62 output intensities (spectrum, hereinafter exemplary showing "M/Z") of M/Z (mass-to-charge ratios) as data (variables) that suggests the presence of chemical substances. Accordingly, data 31, 32, and 33 outputted from the sensors 61 and 62 due to such scanning being continuously repeated and inputted into the conversion unit 131 include information that enables the detected chemical substances to be identified, that is, M/Z that is information (intensity variations, intensity changes) that show (suggest) the detected chemical substances and variations (changes) over time in M/Z. The M/Z values obtained from MS do not completely correspond on a one-to-one basis to the chemical substances that are actually present. However, by providing appropriate rules, it is possible to associate the M/Z with values showing the detected chemical substances on a one-to-one basis. For example, the conversion unit 131 is capable of applying a rule that assigns organic materials with priority over inorganic materials to the M/Z information included in the scan data 33. In addition, the conversion unit 131 can also apply a rule whereby out of organic materials, chemical substances included in the earliest group in an order of functional groups classified using lookup tables (LUT) 133R and 133L is assigned with priority to the M/Z information included in the scan data 33.

FIG. 4 shows a hierarchy for dividing chemical substances into groups (into classes). The first level 81 is chemical class and includes three elements, organic 81a, inorganic 81b, and non-classifiable (unclassified, unknown) 81c. The next level (second level, sub-classes) 82 is divided according to chemical functional groups FG, with organic 81a including 46 functional groups (sub-classes). The next level (third level, substance classes) 83 is a level showing specific chemical substances. One of the functional groups is alkanes (chain saturated hydrocarbons) 82a, with this group 82a including ethane 83a, methane 83b, propane 83c, butane 83d, and the like as chemical substances. The functional groups are not limited to hydrocarbon groups and include an amino group 82b that is one functional group that includes nitrogen, an alcohol group 83c that is one functional group that includes oxygen, a ketone group 83d, and the like. Atomic elements in the molecules of a functional group are subject to the same or similar chemical reactions and may exhibit a common odor and characteristics. Volatile organic materials and organic compounds typically stimulate the sense of smell as odors, and can also be used to monitor health.

Inorganic 81b can be divided into subclasses according to atomic elements. As examples, it is possible to divide into the groups carbon 82e, aluminum 82f, and nitrogen 82g. The third level 83 is a substance level, with carbon monoxide 83e and carbon dioxide 83f being given below carbon 82e.

The unclassified chemical class 81c is provided so that information included in the data inputted from the sensor is not omitted from the RAW data 35. As one example, when an M/Z constituent that has not been assigned to a specified chemical substance is detected, it is possible to assign the intensity variations of such constituent to non-classifiable (unclassified, unknown) 82i, 82j, or 82k and store information for specifying the constituent after the M/Z constituent of unclassified 82i or the like in the header information of the RAW data 35. It is possible to freely increase the non-classifiable sub-classes. In addition, if the chemical substance of a non-classifiable sub-class becomes known at a later time, it is possible to add such class to the sub-classes of a functional group. The division into groups shown in FIG. 4 is merely one example, but is a favorable example of the division of odor data into groups.

FIG. 5 shows one example of a lookup table (LUT) 133 in the generator 130 of the OLP 100 that includes information for assigning the detected chemical substances respectively to specified frequencies. The LUT 133 is one example of a means of defining a frequency space where a plurality of frequencies are respectively assigned in advance to a plurality of specified chemical substances. In place of the LUT 133, it is also possible to define a frequency space using a dictionary file, a database, a library, or the like.

In the LUT 133, as described above, chemical substances are divided into the three classes, organic 81a, inorganic 81b, and non-classifiable 81c on the first level 81, and are defined as being divided into groups FG based on functional groups on the second level 82. In the LUT 133, 48 sub-bands (SB-1 to SB-48) 84 are assigned or allocated corresponding to the plurality of FG on the second level 82. The respective sub-bands have a bandwidth 86 of 950 Hz with a separator of 50 Hz being set between the respective sub-bands. For example, a sub-band SB-1 with a bandwidth (allocated frequency range) from 50 Hz to 1 kHz is assigned to the alkanes 82a FG (sub-class) that includes chemical substances starting with ethane. A 1050 Hz to 2 kHz sub-band SB-2 is assigned to the next FG (sub-class). In addition, a specified frequency f0 that is included in the bandwidth from 50 Hz to 1 kHz of sub-band SB-1 is assigned to a chemical substance, for example ethane, included in the respective sub-classes. A frequency f1 in the sub-band SB-1 is assigned to methane, a frequency f2 in the sub-band SB-1 is assigned to propane, and a frequency f3 in the sub-band SB-1 is assigned to butane. This is the same for other chemical substances.

Accordingly, by referring to the LUT 133, a frequency space in which a plurality of chemical substances classified based mainly on functional groups are assigned to a plurality of frequencies. Therefore, measured values that show the detected chemical substances can be converted to intensities of signals of frequencies corresponding to the detected chemical substances. The converted data is capable of being inversely converted to measured values showing chemical substances by referring to the same definition of the frequency space, that is, the same LUT 133. Note that the definition of the frequency space in which measured values of chemical substances are mapped is not limited to the present embodiment. Chemical substances that are causes of odors are often organic substances with a comparatively low molecular weight. For this reason, a method that assigns specified chemical substances onto a frequency space as shown in the LUT 133 is suited to mapping chemical substances that are the causes of odors onto a frequency space. In other applications, as examples, an application that detects airborne pollutants or an application that determines a health condition from substances included in breath, it is possible to define a frequency space so as to facilitate the mapping of chemical substances that are to be detected by the respective applications.

As shown in FIG. 3, the conversion unit 131 included in the generator 130 of the OLP 100 includes fast sequence mappers (FSM) 132L and 132R that respectively refer to left and right LUT 133L and 133R and map amounts (measured values) showing chemical substances respectively detected by the left and right sensors 61 and 62 onto specified frequencies. In addition, the conversion unit 131 includes waveform shaping units 136L and 136R that respectively convert intensity variations showing the detected chemical substances to intensity signals of frequencies that are assigned by the FSM 132L and 132R using the LUT 133. The respective waveform shaping units 136L and 136R include 48 sub-band wave shaping units (SBWS) 135.1 to 135.48 and are capable of carrying out a wave-shaping process in parallel in sub-band units. The outputs of the waveform shaping units 136L and 136R are the content data 139dL and 139dR in which intensity variations that show detected chemical substances have been converted to intensity variations of specified frequencies.

The content data 139dL and 139dR at this stage is data on frequency regions that are assembled into sub-band units (into each sub-band) and are capable of being assigned appropriate header information 139h and outputted as digital stream data 36 divided into sub-band units. This data can be passed through a QMF for audio data and converted to the same format as data that has been separated into sub-bands.

Figure 6A:
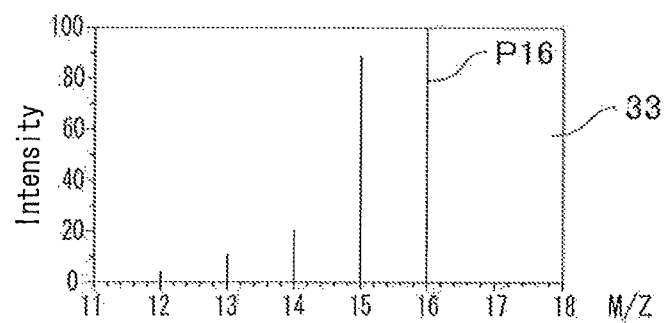
FIGS. 6A and 6B are diagrams showing an example of mapping.
Figure 6B:
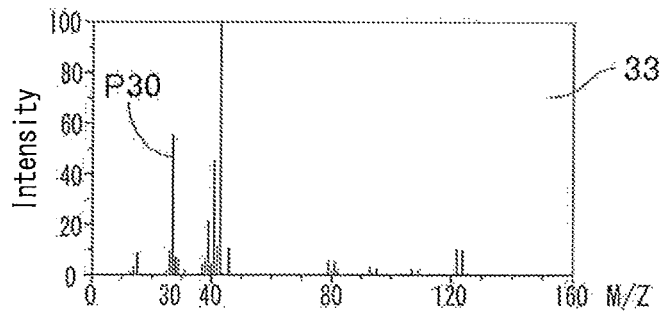

FIGS. 6A and 6B show examples of scan data (MS spectra) 33 that is inputted from MS-type sensors 61 and 62. The M/Z data 16 in FIG. 6A matches the mass-to-charge ratio of methane ($CH_4$). For this reason, the FSM 132L or 132R maps (assigns) a peak P16 of the M/Z data 16 to the frequency f1 included in the sub-band SB-1 of the "alkanes" sub-class (function class) and the waveform shaping unit 136L or 136R converts the intensity of peak P16 to the intensity of the frequency f1.

The M/Z data 30 in FIG. 6B matches the mass-to-charge ratio of ethane ($C_2H_6$). For this reason, the FSM 132L or 132R maps (assigns) a peak P30 of the M/Z data 30 to the frequency f0 included in the sub-band SB-1 of the "alkanes" sub-class (function class), and the waveform shaping unit 136L or 136R converts the intensity of the peak P30 to the intensity of the frequency f0.

The scan data (M/Z data) 33 subjected to conversion may be inputted from an MS-type sensor 61 or 62, or may have been corrected by the preprocessor 121. The FSM 132L and 132R may assign (map) peaks from the scan data 33, which include peaks of fragment ions (ions that become disassociated during the ionization process or flight, also referred to as "daughter ions") and isotope peaks, onto a frequency space without amendment. The FSM 132L and 132R may convert from peaks in the scan data 33 to spectrum data in which constituents detected by an MS are somewhat clarified and peaks of fragment ions and peaks of isotope ions have been removed or reduced so as to assign (map) chemical substances that are probably closer to the actual constituents onto a frequency space.

By mapping onto a frequency space so that all of the peaks included in the scan data 33 are associated to peaks of some kinds of chemical substances, all of the information included in the scan data 33 can be outputted in the content data 139d with no omissions that is included in the RAW data 35. Also, even if a chemical substance has been erroneously assigned to a peak of the scan data 33, it is easy to convert the intensity variations showing the chemical substance to the original intensity variations of M/Z. Since the scan data 33 is preserved, it is not especially important or of little importance whether the generator 130 of the OLP 100 can precisely find the chemical substances actually included in the atmosphere.

FIG. 12 shows the process (step 310) for generating the content data 139d in more detail. In step 311, the buffer into which the scan data 33 is inputted is initialized. The data input buffer is equipped with 32 sample channels, for example. In step 312, the FSM 132L and 132R detect the chemical substances in the data and identify (define) the detected chemical substances. In step 312, the detected chemical substances are defined according to one or a combination of a plurality of methods out of a variety of methods, such as a heuristic method, chemical rules, a hydrogen/carbon ratio rule, and ratio and probability of constituents.

If it is possible to classify a detected chemical substance according to the lookup table 133 in step 313, in step 315 the detected chemical substance is assigned a predetermined frequency of a predetermined sub-band in accordance with the lookup table 133 in the order of chemical class, sub-class, and substance. If the (information on the) detected chemical substance is unclassifiable in the lookup table 133, in step 314, a predetermined frequency of non-classifiable (unclassified) is assigned.

In step 316, the waveform shaping units 136L and 136R convert (map) the intensity of the detected chemical substance to the intensity of the assigned frequency. In addition, a stream generator 137 generates stream-type data, in which digital data on frequency intensity variations have been inserted, in a predetermined stream data format. In step 318, when the inputting of data from a sensor continues, the above processing is repeated, which makes it possible to generate stream-type RAW data 35.

Note that this flowchart shows the processing in the conversion unit 131 as a series of flows to facilitate understanding of the generation method. However, these functions are realized in the conversion unit 131 provided in the OLP 100 by circuits that are capable of parallel processing and the respective processes shown in the flowchart are executed in parallel.

In this way, the OLP 100 is capable of converting information on chemical constituents to a frequency space with higher resolution and high reproducibility. Compounds that are not present in the reference table 133 are tagged in the unknown functional group, which preserves an opportunity for an application or the user to specify an unknown compound using other science and technology. The specified constituent types are represented by respective sub-bands in the content data 139d as pulse trains of the corresponding frequencies. A digital pulse train in the content data 139d expresses variation over time relating to the appearance of a constituent. Note that in the present specification, in the common explanation of the left and right content data 139dL and 139dR, the symbols indicating left and right are sometimes omitted and such data is indicated as "content data 139d". This is also the case for functions and units provided in left and right pairs.

The conversion unit 131 includes a stream generator 138 and outputs data showing intensity variations of frequencies gathered into sub-bands as stream data in a format that is standardized for audio files or image files. The header information 139h includes other information such as environmental information as described below.

2.4 Generation of Stream Data

The content data 139d generated by the conversion unit 131 is data 36 on a frequency region that includes chemical substance information. Accordingly, it is possible to contrast the data 36 with data produced by converting information on a time region, such as audio data and image data, to a frequency region via a FFT. In addition, the generator 130 includes an oscillator 142 and a convertor 141 that converts to data on a time region, for example PCM-type data 34, by carrying out an inverse FFT on the data 36 on a frequency region. In addition, the OLP 100 is capable of outputting both the data 36 on a frequency region and the data 34 on a time region via the interface 107 to the periphery (inside or outside the system 1) as the RAW data 35.

It is also possible to set the scan data 33 obtained from the preprocessors 121 and 122 as data on a frequency region by mapping M/Z information included in the data 33 onto a frequency region and to convert to data on a time region, for example, PCM-type data, by carrying out an inverse FFT. By using the LUT 133 referred to by the FMS 132, it is possible to define M/Z and the frequencies corresponding thereto, and possible to convert M/Z information measured by a mass spectrometer MS to data on a frequency region without converting to chemical substance information. In addition, by carrying out inverse FFT conversion on data on a frequency region, it is possible to convert the M/Z information to data on a time region.

The molecular weight of molecules that are experienced as odors due to their effect on the human sense of smell (olfactory receptor) is said to have an upper limit of 300 to around 400 from the viewpoint of volatility and the like. Accordingly, it is possible to set mass spectrometry results that have a molecular weight in that range as a maximum as a target, and convert the M/Z values included in such mass spectrometry results to a frequency region. In functions or applications including that for stereo images described later, the data mapped onto a frequency space includes not only data produced by mapping chemical substance information, which is converted from M/Z information, onto a frequency space but also data produced by mapping M/Z information onto a frequency space. Similarly, the data on time regions includes data produced by mapping chemical substance information onto a frequency space then inversely FFT and also data produced by mapping M/Z information onto a frequency space then inversely FFT.

The data on time regions can be outputted via the interface 107 and displayed as images on the display 22 or outputted as sound from the speaker 23. Although it is not easy to determine whether such data is meaningful as images and sounds, data with information on the same or similar odors should output the same or similar pattern in images and/or sounds. Accordingly, data that is experienced by the sense of smell may convert to data that is experienced by the sense of sight or the sense of hearing.

The RAW data 35 that includes data 36 on a frequency region or data 34 on a time region can be recorded via the interface 107 into the storage 13 of the system 1. The RAW data 35 can also be transferred via a transceiver unit (communication interface) 17 of the system 1 to outside the system 1. For example, the RAW data 35 is sent though the wireless connection 15 to another terminal, a server and others via a base station on a real-time basis. It is also possible to send the RAW data 35 via a network 401 on a real-time basis to another terminal, a server and others. Recording and reproduction of odor data on a real-time basis is one of the most important characteristics of the OLP 100. Most electronic appliances are capable of exchanging information with a remote user on a real-time basis. One example is an interactive application such as a multimedia application, chat, online learning, and gaming. Each user is capable of exchanging aroma information (odor information) in real time with a remote user by uploading the information onto the Internet or wirelessly transmitting and receiving (downloading) the information.

2.5 Stereo Image

In more detail, the OLP 100 is capable of recording and reproducing odor information in stereo. Data can be inputted into the OLP 100 from the left and right sensors 61 and 62 that have different detection characteristics relating to direction. The conversion unit 131 includes the left and right FSM 132L and 132R and left and right waveform shaping units 136L and 136R. The conversion unit 131 includes a function for mapping scan data 33 obtained from the left and right sensors 61 and 62 or intensity variations showing left and right chemical substances based on the left and right scan data 33 respectively onto left and right frequency spaces. The RAW data 35 of a stereo image includes left and right content data 139dL and 139dR. In the data generation method (step 310), the mapping of the intensity variations showing the left and right chemical substances detected by the data from the left and right sensors 61 and 62 respectively onto the left and right frequency spaces is carried out in parallel.

Stereo sensing (the use of two sensors) is a function that is important in incorporating and emulating the human olfactory function in the system when identifying aroma sources. For example, by carrying out stereo sensing, it is possible to calculate the distance and/or direction to an aroma source. Also, by reproducing odors in stereo, it is possible to provide the distance and/or direction to an aroma source to the user as information. Accordingly, it is possible to provide a three-dimensional method of reproducing odors to the user in the same way as sounds and images. The two sensors 61 and 62 typically aim to capture aroma information from directions that differ by 90 degrees with respect to the center. This is effective in enhancing aroma reproduction and analysis performance that very closely resemble human abilities.

During stereo sensing, the content data 139dL and 139dR detected from the data of the two sensors 61 and 62 may be separately recorded in the RAW data 35, or one of the content data 139dL and 139dR and the difference between the left and right channels may be recorded. The difference can be calculated and recorded in sub-band units. The number of sensors used for stereo sensing is not limited to two and may be three or higher. By disposing a plurality of sensors in three dimensions on the left and right, up and down, or at the front and back, and analyzing the scan data 33 obtained from such sensors, it is possible to identify the positions of the sources of odors more precisely and at high speed.

The sensor controller device 50 is compatible with multisensors and is capable of connecting a plurality of sensors of the same type and/or different types. The device 50 supports dual channels according to IEEE 1451.1, for example. The device 50 supports any combination of sensors and even a differential input, with a typical example being spectrometry-type sensor described above.

The ADC unit 110 of the OLP 100 includes interfaces 111 and 112 for stereo inputs from mass spectrometry-type sensors and ADC 117L and 177R for converting left and right analog data respectively to digital data. In addition, the ADC unit 110 includes an interface 113 for a mass spectrometry-type monaural input, an ADC 117M, and summing amplifiers 119a and 119b for adding the monaural signal to left and right signals. An input from the mass spectrometry-type sensor is inputted into a type-1 preprocessor 121 and subjected to data processing (preprocessing).

In addition, the ADC unit 110 includes an interface 114 for inputting data from a sensor of a different type to a mass spectrometer, and an ADC 117A. An input from a sensor of a different type to a mass spectrometer, for example, a dedicated sensor for detecting a specified chemical constituent is inputted into a type-2 preprocessor 122 and subjected to data processing (preprocessing).

The ADC unit 110 further includes an interface 115 for a digital input, with the digital input being respectively added to the preprocessed signals by summing amplifiers 119c and 119d provided downstream of the preprocessor section 120. The input data 33 for which all the preprocessing has been completed is processed by the conversion unit 131 so that information on chemical substances is converted (mapped) onto a frequency space.

The mixing function of the ADC unit 110 is effective in a number of ways. The external digital input 115 makes it possible for the user to add a background aroma to a video and to add aromas that dynamically changes. Adding a static or dynamic aroma, which becomes a special effect, can be realized by varying a present aroma level to a designated aroma level in the same way as a volume adjustment.

2.6 Inclusion of Supplementary Information Aside from Chemical Substance Information The generator 130 of the OLP 100 is capable of incorporating (convolving) a variety of other information into the RAW data 35 in addition to the content data 139d that is information relating to chemical substances.

2.6.1 Environmental Information (Temperature, Humidity, Pressure)

Temperature, humidity, and pressure have an important role on the action of the sense of smell. To reproduce odors at a time and/or place (remote site) that differ to the time and/or place where the RAW data 35 was generated, it is preferable to correct the intensity of the odor based on information on the temperature, humidity, and pressure.

The ADC unit 110 of the OLP 100 includes an interface 119 that inputs data from sensors (environmental information sensors, environmental information obtaining sensors) that obtain environmental information including temperature and humidity. The generator 130 that generates the RAW data 35 includes a supplementary information encoder (supplementary information adding unit) 137 that obtains environmental information when the RAW data (first data) 35 is generated and includes such information in the header information 139h in the RAW data 35 as environmental information for when the RAW data 35 was generated. The stream generator 138 adds the header information 139h that includes the supplementary information to the content data 139d to generate a data stream and outputs the result as the RAW data 35.

In the process that generates the RAW data 35 (step 310, see FIG. 12) the conversion to a stream in step 317 also includes the incorporation of the environmental information generated at that time into the RAW data 35. Data on temperature, humidity (relative humidity), and atmospheric pressure are recorded in real time together with the content data 139d in the RAW data 35. This means that the environmental information will not be omitted from the data and that during reproduction, there is no need to synchronize the environmental information, which makes it possible to improve the reproduction efficiency of odor data.

2.6.2 Air Flow

The OLP 100 is capable of adding data of an air flow sensor 74 to the header information 139h as supplementary information. The information of the air flow sensor 74 adds a property as information with greater directionality to the RAW data 35 in addition to the stereo sensing. Accordingly, in a security application, it is possible to accurately determine the direction of a pollutant source and wind direction, which makes it possible to assist in rescuing the user from danger and preventing the user from approaching danger from the outset. In a robotic engineering application, the OLP 100 that supports an airflow sensor is capable of providing a robot with a function for identifying the direction of and distance to an aroma source.

2.6.3 Time

The OLP 100 is capable of also adding date/time data to the header information 139h as supplementary information. Date/time information is effective as proof of the generation of the RAW data 35. The OLP 100 is capable of including absolute time and/or relative time information in the header information 139h as metadata. A relative time is elapsed time from a start of reproduction, for example, and is effective as information for synchronizing the release of aroma data when reproducing the aroma data together with other multimedia content.

2.6.4 Position

The OLP 100 is also capable of adding position information to the header information 139h as supplementary information. The position information is effective as proof of the generation position of the RAW data 35. The OLP 100 is capable of including absolute position information and/or relative position information in the header information 139h as metadata. One example of absolute position information is information on a position produced by satellite positioning that can be obtained by the GPS system 19, such as latitude and longitude data. One example of relative position information is information on a base station when access is carried out by mobile telephone.

In addition, in an application such as a virtual world or game, it is possible to set a virtual position in the position information. For example, it is possible to release an odor to show that the user has arrived at or is present at that position in such virtual world or game. The information that can be incorporated in the RAW data 35 is not limited to the information described above. For example, by combining image information obtained by the camera 24 and/or sound information obtained by the microphone 25 with the odor information 34 or 36, it is possible to generate and output multimedia information that also includes odors as the RAW data 35. Such multimedia RAW data 35 may be static data on a "one-shot" basis or may be dynamic data for a time region.

2.6.5 RAW Data Stream

One example of the RAW data stream 35 is raw data (i.e., data that has not been subjected to processing such as compression and encryption) where sub-band signals on odors are linked. The RAW data 35 includes a supplementary channel for environmental variables such as temperature, with it being possible to further include variables such as humidity, air pressure, and airflow in the supplementary channel. The RAW data 35 is capable of storing data that change over time and relate to single, monaural, or stereo (left-right) sense of smell as stream-type data. A typical data stream includes the header 139h and data packets of the payload (content data) 139d. The stream header 139h also includes a time stamp, data format, divisions (packetized specification), and other important items for signal processing.

The RAW data stream 35 fundamentally includes information corresponding to all of the constituent types that are specified by a sensor (capture device). The OLP 100 is designed with consideration to universal applicability for how the RAW data 35 may be used, and does not exclude information on compounds or the like detected by a sensor from the RAW data stream 35 regardless of whether such information relates to the human odor space. This is because there are a great variety of applications such as real time monitoring that are targeted at the environment, health, and pollution. On the other hand, the compression engine 160 of the OLP 100 may be configured so as to exclude information relating to chemical substances that are outside the human odor space.

Through an olfactory stimulus, the RAW data stream 35 is capable of providing the user with a rich experience. Humans are capable of detecting the source and the direction of an aroma. The human brain uses quantitative measurements to determine an aroma source. It is possible for the RAW data stream 35 to include almost all information that stimulates the human sense of smell.

In addition, this characteristic is important in robotic engineering and artificial intelligence. It is possible to issue the user with a warning to enable the user to escape from danger such as a fire, a dangerous gas leak, or a biohazard. Position information produced by GPS can be used to assist in determining whether the user should evacuate. By applying the OLP 100, it is possible in the field of robotic engineering to add an odor recognition function to a robot in addition to image recognition and voice recognition. By also adding the sense of touch, it is possible to equip a robot with four senses (sight, hearing, touch, and smell) out of the five senses. This means that it is possible to provide a robot that is capable of recognizing things (objects, people) and recognizing the peripheral state using a plurality of senses that include odors.

The plurality of senses that also include odor have roles that complement one another in helping a robot recognize things and/or the peripheral state. When recognition using image information, voice information, and/or a sense of touch alone is difficult or such recognition would require a long time, the addition of odor information makes it possible to improve the recognition precision and speed. Also, during pattern recognition of odors that is described below, it is possible to limit or reduce a range (search range/space) for pattern recognition using or help of image information, voice information, and/or sense of touch, which makes it possible to improve the precision and speed of pattern recognition of chemical substances in the OLP. A recognition function that recognizes things (objects, environment, and the like) through cooperative use of odor information, image information, and/or voice information is effective not only in a robot but also in a mobile telephone or the like equipped with a function that obtains such information.

Figure 7:
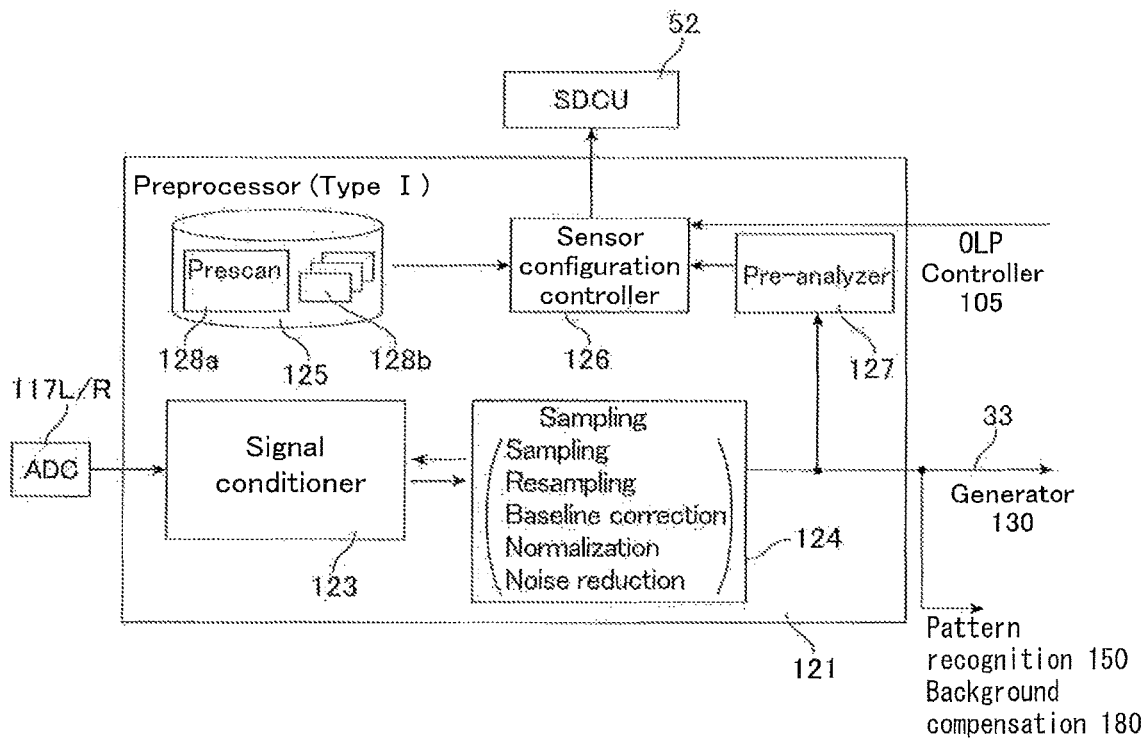
FIG. 7 is a block diagram of a preprocessor.
Figure 8:
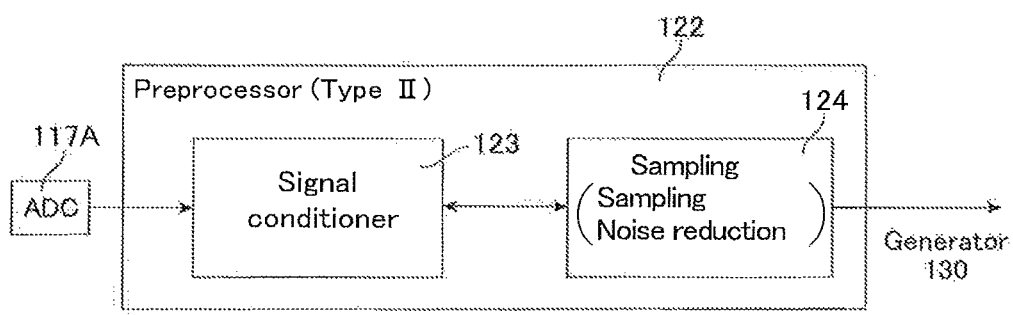
FIG. 8 is a block diagram of a preprocessor of another type.

2.7 Preprocessor (Reconfiguration of Measurement Conditions) (FIGS. 7, 8)

The OLP 100 includes the preprocessor section 120 that carries out preprocessing of the input data from a sensor. A typical preprocessor 121 carries out resampling, baseline correction, normalization, noise reduction, and peak detection. By converting preprocessed data to the RAW data 35, the OLP 100 makes it possible for chemical constituents to be analyzed on the Web or by a PC using an MS (mass spectrometry) database such as NIST or Wiley. One characteristic of the preprocessor 121 of the OLP 100 is automatic control of measurement conditions of a spectrometry-type sensor (analysis-type, spectroscopic or spectrometric sensor or detector).

FIG. 7 is a block diagram of a typical preprocessor 121. The sensors 61 and 62 can use spectrometry or analysis-type sensors which, like a mass spectrometry apparatus, have a sensitivity, resolution, and selectivity that can be controlled according to setting conditions. The preprocessor (preprocessing apparatus) 121 automatically sets the setting conditions of a sensor. The preprocessor 121 first sets a preliminary detection condition 128a for scanning a wider range in a spectrometry-type sensor and carries out preliminary analysis on the preliminary detection results. Next, based on the substances found by the preliminary analysis, a setting condition 128b suited to the application is selected and the setting condition of the sensor is changed. The preprocessor 121 periodically sets the preliminary detection condition 128a and carries out the preliminary analysis.

In the generation method of the RAW data 35 by the OLP 100 shown in FIG. 11, once sensor data has been inputted from the sensor controller device 50 (step 301), the data is digitized by the ADC unit 110 (step 302) and the sensor conditions are then reset (reconfigured) by the preprocessor 121 (step 330). The detailed operation of the resetting (step 330) is shown in the flowchart in FIG. 13. After this, main sampling (re-sampling) is carried out (step 303a) and after the elapse of a certain period of time, a resetting process 330 is repeated in step 303b. By periodically resetting the measurement conditions of the sensor, it is possible to obtain data with conditions that are suited to the time and location. In the process (step 310) that generates the RAW data 35, information on chemical substances detected by data measured according to conditions that are suited to the time and location can be set as stream data. That is, the process that generates the RAW data 35 further includes setting the setting condition at the preliminary detection condition 128a that scans a wider region in the spectrometry-type sensor (spectroscopic of spectrometric sensor), carrying out preliminary analysis on the preliminary detection results, and changing the setting condition based on the substances found by the preliminary analysis.

More specifically, the preprocessor 121 includes a signal conditioner 123 that improves the state of scan outputs (spectrograms) of the sensors 61 and 62 and a sampling unit 124 that samples peaks included in mass spectra in scan cycles. The sampling unit 124 generates data on a chemical substance space, for example, PCM-like data on intensity relative to M/Z. When doing so, the sampling unit 124 carries out baseline correction, normalization, noise reduction, and peak detection.

Baseline Correction

The sensor data (spectrogram) 32 includes a baseline that fluctuates due to factors such as chemical noise and ion overloading. The sampling unit 124 estimates a low-frequency baseline that is hidden by high-frequency noise and signal peaks and subtracts a low-frequency constituent (component) that is regarded as the baseline from the spectrogram 32.

Normalization

The sampling unit 124 standardizes (normalizes) the spectrogram 35 by rescaling the maximum intensity of each signal according to requests or rules set by an application.

Noise Reduction

The normalized data will normally include a mixture of noise and signals. Noise reduction is required to improve the precision and validity of the spectrum, and reducing noise can enable a peak detection algorithm to operate more effectively. One type of noise reduction is a polynomial filter that is able to maintain the sharpness of peaks.

Peak Detection

The peak detection algorithm specifies peaks based on amplitude. Since additional information is also included in the shapes of the peaks in a spectrum, this is also taken into consideration. Since the shapes of peaks are also characteristic, it is possible to specify individual peaks (individual chemical substances (molecules, compounds, constituents) by using a shape matching function and changing the scale and amplitude. This technique is a plain or simplified form of pattern matching, but is capable of specifying signals that have been effectively separated from spike noise and other noise.

Re-Sampling

The preprocessor 121 further includes a sensor configuration control unit 126, a library 125 that includes a plurality of conditions (measurement conditions) that can be set in a sensor, and a preliminary analysis unit 127. The mass-spectrometry-type sensors 61 and 62 typically obtain substantially the same resolution across the wide range of the spectrum, with it being possible to set a low-resolution mode that is capable of comparing the intensities of chemical substances across a wide range and a high-resolution mode with high resolution where there is an increase in the amount of redundant data. The low-resolution mode condition 128a is suited to preliminary measurement (preliminary detection), and the high-resolution mode 128b is used to measure data that are converted to the RAW data 35. More specifically, according to the conditions 128a, 128b, it is possible to change the voltage of the mass-spectrometry-type sensors 61 and 62 for scanning the M/Z (and thereby change the scan speed) and to change the voltage used for ionization.

Typically, the sensor configuration control unit 126 obtains a spectrum of a wider range by setting the low-resolution mode 128a in the sensors 61 and 62 via the SDCU 52 of the sensor controller device 50. The preliminary analysis unit (pre-analyzer) 127 obtains preliminary analysis data via the sampling unit 124 and limits the spectrum region (range) in which the chemical substances requested by an application will be detected. The preliminary analysis unit 127 may set the conditions so that a spectrum region with a lot of noise is not measured. The sensor configuration control unit 126 sets the high-resolution mode 128b with conditions that facilitate detection of the target chemical substances via the SDCU 52 into the sensors 61 and 62. However, depending on the application, there are a variety of conditions, such as prioritizing a wide spectrum or prioritizing a temporally high resolution, and high-resolution mode is not limited to being suited to a condition for obtaining an input for generating the RAW data 35.

The technique of periodically carrying out a preliminary measurement (initialization of measurement) and dynamically reconfiguring the measurement conditions of a sensor is one of the major characteristics of the OLP 100. The analyte and/or recording target that is subject to interest and included in the RAW data 35 is defined according to the application. For example, a regulatory agency or control agency may aim to record the concentration of a pollutant or a harmful compound in the air, and it is possible to set a mass spectrum for the target substance and/or compound in advance. In another application, it may be important to distinguish between a target aroma and a background aroma that is not desired, with it being possible to provide the OLP 100 in advance with the spectrum of the chemical substances in question.

The OLP 100 analyzes preliminary samples, constructs a dynamic table of compounds that can be measured and defines the conditions for resampling with consideration to the objectives of an application, with consideration to environmental variables, and with consideration to the intensities of the left and right channels. This dynamic reconfiguration technology is effective in identifying and excluding background noise during measurement. This dynamic reconfiguration technology is capable of greatly increasing the overall performance, sensitivity and selectivity for measurement and detection relative to the processing performance of the circuitry of the OLP 100. This dynamic reconfiguration technology can be applied only to a spectrometry-type measurement sensor such as a spectrometer or an optical sensor.

Figure 13:
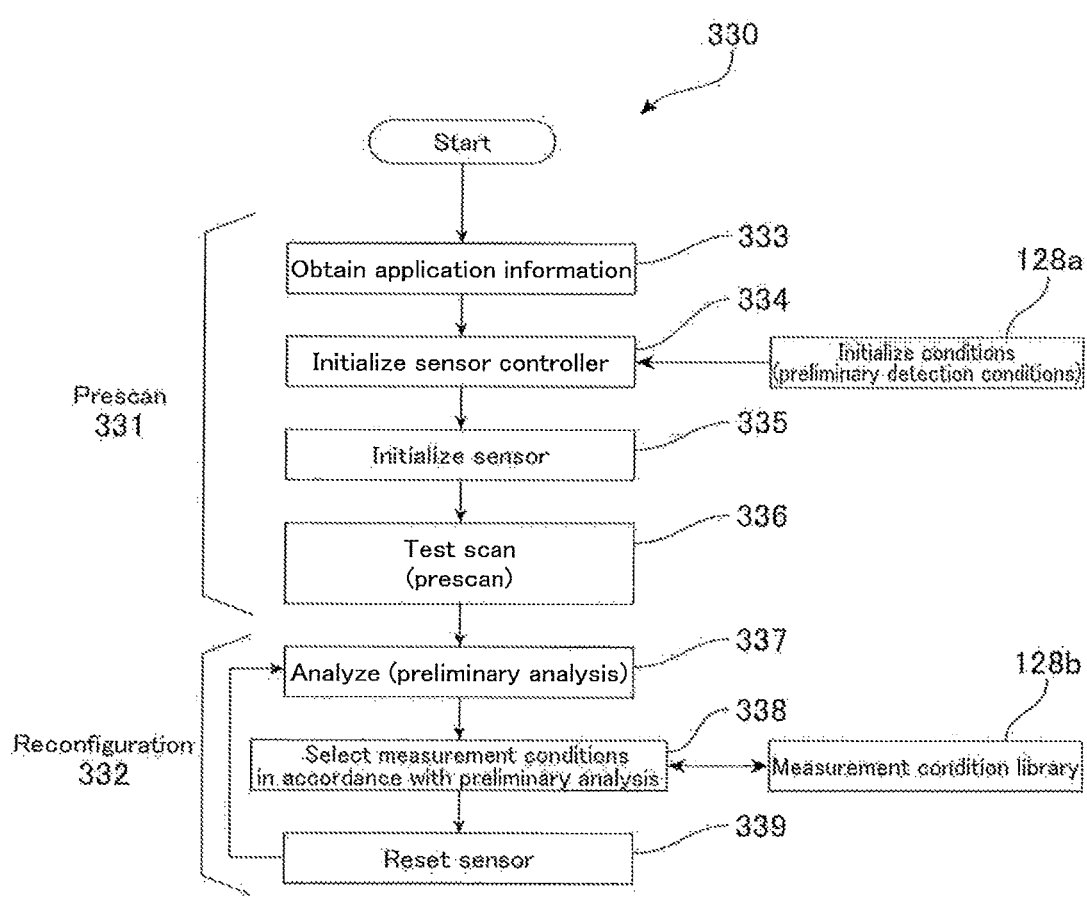
FIG. 13 is a flowchart showing the process of a sensor reconfiguration.

FIG. 13 is a flowchart showing the process (step 330) that dynamically reconfigures a sensor. This step 330 includes a prescan step 331 and a reconfiguring step 332. The prescan 331 includes a step 333 of obtaining measurement conditions from an application, a step 334 of initializing a sensor controller (SDCU) 52, a step 335 of resetting each sensor to initial conditions, and a step 336 of carrying out a test scan.

In the step 333 that obtains the measurement conditions from the application, conditions that are suited to an application or are defined by an application such as the recording of odors, pollution monitoring, and health monitoring are obtained and stored in the library 125. In the step 334 that initializes the sensor controller 52, if a plurality of types of sensors are connected to the sensor interface 51, an optimal sensor is selected or priorities are set for the sensors. Also, the condition 128a for preliminary measurement is obtained from the library 125. This condition may include not only a condition that initially sets a sensor but also an instruction, such as displaying a scan on the display of the system 1. In the step 335 that resets the respective sensors using initial conditions, the initial setting may include not only mass spectrometry-type sensors but also sensors that measure temperature and humidity.

The reconfiguring step 332 includes a step 337 of carrying out preliminary analysis on the results of a test scan, a step 338 of selecting the measurement condition 128b in accordance with the preliminary analysis, and a step 339 of resetting the sensor controller 52. In the step 337 that carries out preliminary analysis, it is possible to analyze not only the spectrogram 33 but also other conditions such as left-right difference, temperature, humidity, and airflow. In step 338 that selects the suitable measurement condition 128b, a plurality of conditions are selected as a foreground condition and a background condition, and by driving a sensor using such plurality of conditions according to time division (time sharing), it is possible to go together multiple conditions and achieve a good balance between a high resolution for detecting chemical substances and a temporally high resolution for intensity variations.

FIG. 8 is a block diagram of the preprocessor (second-type preprocessor) 122 for a sensor of a type where the measurement conditions of the sensor cannot be controlled automatically. The preprocessor 122 includes a signal conditioner 123 and a sampling unit 124.

2.8 Accommodating Sensors of Multiple Types

Another different characteristic of the OLP 100 is the ability to accommodate a plurality of types of sensor and to aggregate the measurement results of such sensors in RAW data 35 of the same format. That is, the conversion unit 131 of the generator 130 includes a function that maps the intensity variations showing chemical substances detected using the data respectively from the plurality of sensors onto a common frequency space. The generating process 310 includes the mapping of intensity variations, which show the chemical substances that have been clarified from the data respectively received from the plurality of sensors, onto the same frequency space.

Even if the type of sensor differs, the outputs of sensors that detect chemical constituents will be chemical constituents. Accordingly, by referring to the lookup table 133, the FSM 132 is capable of mapping the detection result of a sensor onto one of the frequencies in a frequency space. This means that by converting chemical substances to data, the OLP 100 provides an interface with extremely wide applicability. Also, the RAW data 35 generated by the OLP 100 is capable of being converted to data with wide applicability without depending on the sensor type.

The OLP 100 is intentionally designed to function as a single chip olfactory processor for capturing odors and producing a data stream suited to computing and electronic apparatuses. The user is capable of using a variety of types of gas sensors to capture odors. By being used together with the OLP 100, FAIMS (Field Asymmetric Waveform Ion Mobility Spectrometry) is most suited to odor processing that is capable of obtaining high resolution data. However, other sensors can also be connected to the OLP 100, as one example, to achieve a low-end application, the user is capable of connecting a SAW, a liquid crystal microbalance, a polymer or other sensors that are compliant with IEEE 1451. Although the OLP 100 fundamentally provides an interface for IEEE 1451 and spectrometry-type sensors, it is simple to add an interface corresponding to sensors of another arbitrary type and to add a convertor.

The OLP 100 should preferably be equipped with a function that obtains the characteristics of a sensor connected to the sensor interface 51 during device initialization. An array-type sensor is a group of a plurality of sensors that are sensitive to a specified group of chemical constituents and the constituents themselves, and a mass spectrometry sensor functions according to the principles of mass time of flight (TOF) and ionization techniques. Sensors of respective categories are sensitive only for purpose of certain applications. Although a large number of sensors have a tendency for the detection results to drift according to temperature and humidity, the RAW data 35 is capable of correcting or compensating for such drift. In addition, although there is a tendency for the reaction speed and solubility of aromatic compounds to change in accordance with temperature and humidity, the RAW data 35 is capable of correcting or compensating for this tendency.

In this way, the RAW data 35 that is supplied by the OLP 100 is applied to a common signal format irrespective of the properties of the capture device, with it also being possible to incorporate a variety of other conditions and metadata relating to odors in a data stream. Since the RAW data 35 is converted or assigned (mapped) onto data in a frequency space or time space, it is possible to apply digital signal processing techniques to improve or increase the functionality of the obtained signals, data or information. One example of digital signal processing that can be applied is filtering, which is important in upgrading, compression and pattern matching of signals. Another example of digital signal processing that can be applied is predictive processing (error theory, extrapolation technology) that is applicable to signal correction when recording and transferring data. These are also important characteristics and advantages of the OLP, one objective of which is to enable a machine olfactory function.

Figure 9:
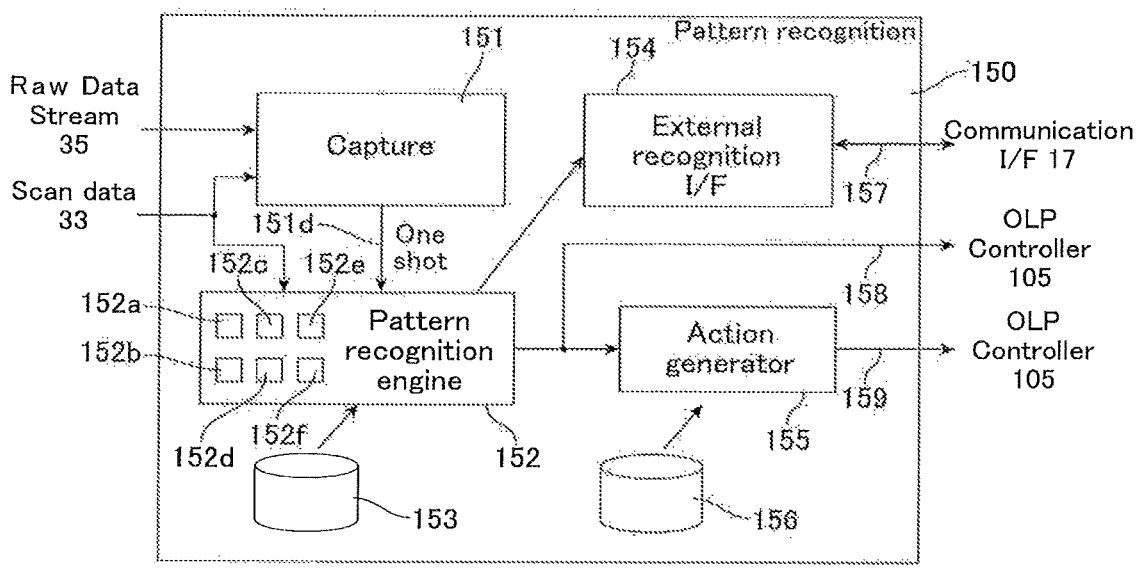
FIG. 9 is a block diagram of a recognition section.

3. Substance Recognition by OLP (FIG. 9)

By subjecting the content data 139$d$ in which chemical substance information has been mapped onto a frequency space to pattern matching with target substance information that has been mapped onto the frequency space, it is possible to specify substances included in the content data 139$d$. The content data 139$d$ is also capable of specifying substances by inverse conversion into an M/Z space.

The OLP 100 includes the recognition section 150 and the recognition section 150 incorporates a capture unit 151 that generates static data 151$d$ from the RAW data (first data) 35 and recognizes specified substances based on the static data 151$d$. The RAW data 35 is stream-type data with little temporal locality and the capture unit 151 generates "one-shot"-type static data 151$d$ with temporal locality for use in data analysis and recognition. The capture unit 151 may be included in the OLP 100 as a service function that is independent from the recognition section 150 and can be used to generate, from the RAW data 35, static data for processing of another application, such as printing.

The recognition section 150 includes a library 153 that includes a plurality of recognition target patterns in which chemical substances included in a plurality of target substances are mapped in advance onto a frequency space individually or in a mixture, and a recognition engine 152 that carries out pattern recognition on static data by referring to the library and outputs the recognized target substances. One example of the recognition engine 152 is an engine that carries out pattern recognition in units of sub-bands. The recognition result 158 is transferred to the OLP controller 105 and is transmitted to the system 1 in accordance with a sequence provided in the OLP controller 105. Based on the recognition result 158, a suitable application that runs on the system 1 may issue a warning via the display and sounds, and/or may carry out statistical processing and/or recording.

The recognition section 150 can include a function that specifies substances by inversely converting the content data 139$d$ included in the RAW data 35 to an M/Z space. In this case, in place of the content data 139$d$, it is possible to specify substances from the scan data 33 that includes the M/Z information. In the library 153, it is preferable to provide a plurality of recognition patterns (M/Z patterns) in which chemical substances included in a plurality of target substances have been mapped in advance either independently or in a mixed state onto an M/Z space. The scan data 33 may be one-shot data and when the scan data 33 has been converted to data of a time region by an inverse FFT, it is possible to convert the data to static data using the capture unit 151.

The recognition section 150 further includes an external recognition interface 154 that outputs, via the communication interface 17, the static data 151$d$ or data 157 produced by converting the static data for pattern recognition and obtains information relating to the recognized substances. The recognition section 150 includes an action generator 155 that generates a specific action from the recognized substances and an action library 156, with the generated action 159 being transmitted to the OLP controller 105.

In this way, the OLP 100 does not merely generate the RAW data 35 but also includes capturing the static data 151$d$ from the RAW data 35 and recognizing specified substances based on the static data 151$d$, and therefore provides a method for examining, investigating, and diagnosing a variety of phenomena.

The pattern recognition engine 152 is used for local applications such as odor analysis, health monitoring, pollution, and keeping safety (security). The pattern recognition engine 152 includes a feature (characteristic) extraction processing block 152$a$, a dimensionally reduction processing block 152$b$, a classification processing block 152$c$, a neural network processing block 152$d$, a database search engine 152$e$, and a machine learning functional block 152$f$.

Pattern Recognition Using Sub-Bands

The content data 139$d$ includes chemical substance information that is assigned to a plurality of sub-bands respectively. Accordingly, it is possible to perform pattern recognition in each sub-band (sub-band units) and possible to greatly reduce the factors handled by the respective pattern recognition processes to a fraction of one over several tens. Pattern recognition in sub-band units makes it possible to improve the processing speed for recognizing specified substances, and also makes it possible to reduce the processing performance of the pattern recognition engine 152 required to do so. The respective processing blocks described below can be implemented and/or carried out for each sub-band.

Feature Extraction Processing Block 152$a$

The feature extraction processing block 152$a$ is a block for implementing linear, non-linear, and heuristic algorithms. The content data 139$d$ included in the RAW data 35 is information in which a mass spectrogram outputted from the preprocessor 121 has been mapped onto a frequency space using chemical substances as indexes. Accordingly, the content data 139*d* includes information that is redundant and was multiplexed fundamentally due to the large number of chemical substances. To process the content data 139*d* that exhibits redundancy and is multiplexed, the pattern recognition engine 152 needs sufficiently high processing performance. To cope with the redundancy of the data, it is preferable for the recognition engine 152 to include an algorithm based on a suitable signal model. It is also possible to apply a standard algorithm such as principle component analysis (PCA) or a discriminate analysis (linear discriminate analysis, LDA) to extract characteristics.

Pattern Classification Processing Block 152*c*

The pattern classification processing block (pattern classifier) 152*c* includes a classification algorithm, such as a quadratic, universal approximation, or KNN (K Nearest Neighbor), that is easy to implement in a computer. The pattern classification processing block 152*c* classifies odor vectors into corresponding classes.

Neural Network Processing 152*d*

The recognition engine 152 includes neural network processing 152*d* and can apply a neural network to pattern matching. A neural network and fuzzy logic algorithm decide the characteristics and patterns of odors in real time. Neural networks are likely to form the core of artificial intelligence. In the OLP 100 also, since the neural network is capable of simulating a number of unique characteristics of the human brain, this is suited to reproducing the human sense of smell. By carrying out training and learning, a neural network can increase the speed of pattern matching for a plurality of odor patterns (fingerprints) stored in advance in the library 153. It is also possible to store a new fingerprint as a target in the library 153. In addition, it is also possible to obtain a new fingerprint from the Web via the external interface 154 and widen the range of pattern matching to include fingerprints provided on the Web, for example, on a server or a home page.

Machine Database and Machine Learning

The pattern recognition engine 152 includes a CAM-based hardware lookup engine (database search engine) 152*e* for searching the pattern database 153 at high speed. If the pattern recognition engine 152 succeeds to find a match in a local database 153, the pattern recognition engine 152 sends the odor pattern and characteristics back to the OLP controller 105. The OLP 100 is not limited to searching (recognizing) odors, and can carry out recognition of substances that may affect the human body and/or may be dangerous even if such substances have little effect on the sense of smell. In addition, the pattern recognition engine 152 provides the user with a learning function block 152*f* that trains the system to recognize or learn a new odor pattern or with an interface for such purpose. Any material whose composition or constituents are established by a mass spectrometer or any material registered in a standard chemical database is registered in the database 153 as a target odor or substance pattern with generating a pattern by mapping the constituents of the target substance onto the frequency space using the lookup table 133.

Figure 10:
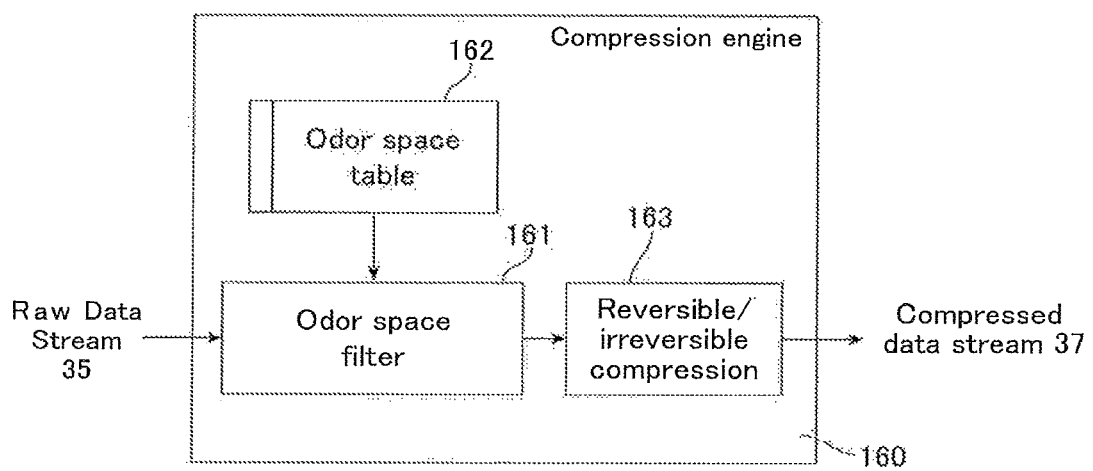
FIG. 10 is a block diagram of a compression unit.

4. Data Compression by OLP (FIG. 10)

Signal compression is one of important functions in reducing the bandwidth required for transmission and reducing the recorded volume. The OLP 100 includes the compression apparatus (compression unit) 160 for generating the compressed data 37 produced by compressing the RAW data (first data) 35. The compression unit 160 includes a compression control unit 161 that changes the compression conditions according to the sub-band. One example of a compression control unit for content data 139*d* relating to odors is an odor space filter 161. Based on information in an odor space table 162, the odor space filter 161 increases the compression ratio by deleting sub-bands assigned to groups not related to odors out of the plurality of sub-bands included in the RAW data 35. By excluding signals that are present outside the human odor space, it is possible to reduce the data amount without lowering the amount of information on odors for human.

Then, the sub-bands related to such odors are compressed using a reversible (lossless) algorithm or are compressed by an irreversible (not lossless) algorithm by a reversible/irreversible compression unit 163. The odor space filter 161 divides or separates the plurality of sub-bands included in the RAW data 35 into sub-bands assigned to groups that are unrelated to odors and sub-bands assigned to groups related to odors, and by having the reversible/irreversible compression unit 163 apply an irreversible compression method to sub-bands that are unrelated to odors and apply a reversible compression method to sub-bands that have been assigned to groups related to odors, it is possible to raise the compression ratio without lowering or less lowering the amount of information. The reversible/irreversible compression unit 163 is also capable of compressing the entire RAW data 35 using a reversible algorithm or compressing the entire RAW data 35 using an irreversible algorithm.

The data that has been compressed by the compression unit 160 is converted to the encrypted data 38 by the encryption unit 169 and is supplied to the system 1 via the OLP interface 107. In the system 1, it is possible to record the data 38 in the storage 13 and transfer the data 38 to the outside via the communication unit 17.

Irreversible compression that deletes some of the sub-bands is one of important characteristics of the OLP 100. It is possible not only to remove sub-bands that are unrelated to odors, but also to compress data using the characteristics of the human sense of smell. For example, odors with a low intensity may be hidden by odors with high intensities that occur at the same time. Information showing such odors can be excluded from the stream 37 after compression to raise the compression ratio. The compression unit (compression engine) 160 may provide an interface for defining a quality aspect to the user or an application. The user or application can negotiate and decide the quality aspect of the stream 37 compressed in keeping with the functions of the target device, storage capacity, or network bandwidth. The compression/encode unit 160 is capable of dynamically changing the quality of the compressed data stream 37 based on such elements.

One typical compression/encoding algorithm is entropy encoding. It is easy to use other compression formats, and in particular compression formats defined according to a standards body or a standard-setting organization such as ISO or MPEG. The compressed data stream 37 is outputted in packets that include a header and a payload, with the header including information that is required by a decoder to decode the stream.

In FIG. 11, an overview of the processing of the encoder section 101 of the OLP 100 is shown using a flowchart. When data has been inputted from a sensor or sensors in step 301, the data is digitized in step 302. In step 330, the conditions of the sensor are dynamically reconfigured and sampling is carried out in step 303*a*. The RAW data 35 is then generated in step 310. If recognition of the substances included in the RAW data 35 is requested by an application (step 304), substances are recognized by the recognition section 150 (step 305). If compression of the RAW data 35 has been requested (step 306), the data is compressed by the compression/encode unit 160 (step 307). In addition, if output of the RAW data 35, the compressed data 37, and/or compressed and encrypted data 38 has been requested (step 308), such data is outputted from the OLP interface 107 to the system 1 (step 309).

5. Data Reproduction and Output by OLP

As shown in FIG. 2, the OLP 100 includes the reproduction apparatus (decoder section) 102 for converting the content data 139$d$ of the RAW data 35 to odor data 39 and supplying the odor data 39 to the driver 201 of the odor generating apparatus 200. The device driver 201 includes a function that converts the odor data 39 to a combination of odor sources 202 that are capable of being used in the odor generating apparatus 200. The decoder section 102 includes a decryption unit 173 that receives and decrypts the encrypted data 38, a reproduction analysis unit (parser) 170 that analyzes the decrypted data 37, and a decompression (expansion) unit 175 that decompresses the data 37 to restore (reconstruct) the RAW data 35 according to an appropriate method based on the result of the reproduction analysis unit 170.

If the environment when the RAW data 35 was recorded and the environment when odors are reproduced according to the RAW data 35 are exactly the same, it is possible to output the content data 139$d$ stored in the RAW data 35 as the odor data 39. However, since the time/date and the place during recording differ to the time/date and the place during reproduction, it is very rare for the environments to match. For this reason, the decoder section 102 includes the compensation (correction) unit 180. The compensation unit 180 includes a function (first compensation function, first correction function) that generates odor data 39 that has been compensated in accordance with environmental conditions such as temperature and a function (second compensation function, second correction function) that generates odor data 39 that has been corrected in accordance with background odors.

That is, the compensation unit 180 includes a function as a first compensation unit that obtains environmental information during reproduction from the sensor group 70 that obtains environmental information in the form of temperature, humidity, and atmospheric pressure, compares such environmental information with the environmental information during generation, and converts the content data 139$d$ to the odor data 39 that is suited to the environmental information during reproduction. The environmental information during reproduction corresponds to environmental information included in the header information 139$h$ of the RAW data 35.

In addition, the compensation unit 180 includes a function as a second compensation unit that obtains information on chemical substances during reproduction based on intensity variations showing chemical substances detected by the data from the sensors 61 and 62, compares such information with the content data 139$d$ of the RAW data 35 (that is, the information on the chemical substances when the RAW data was generated), and converts the content data 139$d$ to the odor data 39 that is suited to the information on the chemical substances during reproduction.

In addition, the decoder section 102 includes a reconstruction unit 190 that converts the content data 138$d$ to the odor data 39 based on the characteristics of the human sense of smell. The odor data 39 reproduced or generated in this way is data that uses standardized chemical substances as indices. Accordingly, by providing in advance a lookup table or function that is capable of converting a combination of standardized chemical substances that have the potential of being included in the odor data 39 to a combination of unique odor sources in the odor generating apparatus 200, the device driver 201 is capable of reproducing odors transmitted by the RAW data 35 using the odor generating apparatus 200. The decoder section 102 includes stereo reproduction function (unit) and supplies left and right odor data 39 to the device driver 201 of the reproduction apparatus 200 that includes reproducer of left and right odors.

Figure 14:
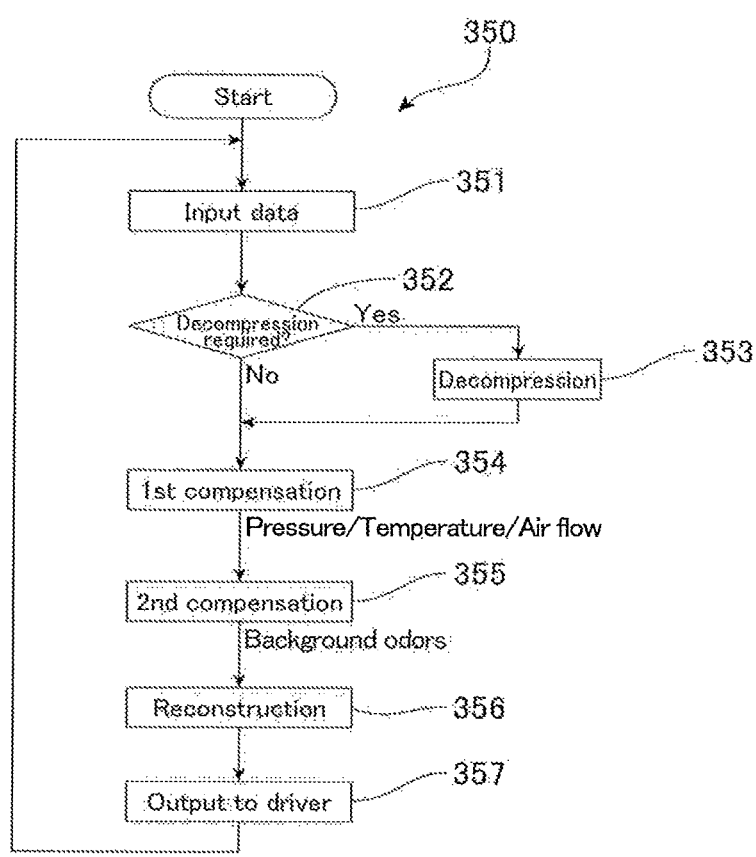
FIG. 14 is a flowchart showing a reproduction process.

FIG. 14 shows an odor reproduction process 350 by the OLP 100 by way of a flowchart. In step 351, the RAW data (first data) 35 including the content data 139$d$, the compressed data 37, and/or the data 38 that has been compressed and encrypted is received. If data extraction is required in step 352, in step 353, the extraction is performed by the decryption unit 173, the reproduction analyzing unit 170, and the decompression unit 175 to restore the RAW data 35.

In step 354, the compensation unit 180 compares the environmental information during reproduction with the environmental information included in the RAW data 35 and converts the content data 139$d$ to odor data 39 that is suited to the environmental information during reproduction (first background compensation process). In step 355, the information on chemical substances during reproduction is compared to the content data 139$d$ and is converted to odor data suited to information on chemical substances during reproduction of the content data 139$d$ (second background compensation process).

In addition, in step 356, the content data 139$d$ is converted to the odor data 39 by the reconstruction unit 190 based on the characteristics of the human sense of smell. The odor data 39 generated in this way is supplied to the device driver 201 in step 357.

The compensation unit 180 and the reconstruction unit 190 also permit a user to manually alter the aromas to be reproduced. In addition, the compensation unit 180 and the reconstruction unit 190 permit an application or other multimedia content to alter the aromas to be reproduced. The reconstruction unit 190 reconstructs the odor data 39 by applying a number of rules that are based on the sense of smell, such as not reproducing aromas that are below a level that can be felt by humans and increasing the level of an aroma when the human sense of smell is saturated. The reconstruction unit 190 includes a function that is operable when a user profile has been set to raise or lower an aroma level so as to match the user's preference, olfactory ability, sensitivity, or the like.

6. Various Supplementary Information about OLP

The OLP 100 should preferably be provided as a chip (integrated circuit device) in which the circuits included in the generation apparatus (generator) 130 are integrated. All of the functions of the OLP 100 described above may be realized by an integrated circuit, some of the functions may be realized by firmware (a program or program product), some of the functions may be realized by functions of the system 1, and some of the functions may be realized by functions on the Internet. The functions of the OLP 100 may be realized by fixed circuits or may be realized by dynamically reconfigurable circuits. It is possible to provide a program (program product) for realizing some or all of the functions of the OLP 100 using a computer, to provide such program recorded on an appropriate recording medium such as a CD-ROM, and to provide such program via a communication medium such as the Internet.

Although the OLP 100 includes the encoder section 101 that generates data and the decoder section 102 that reproduces data, the OLP 100 may be a dedicated reproduction processor that does not include the encoder section 101 or a dedicated generation processor that does not include the decoder section.

By using the OLP, it is possible to implement an olfactory port for capturing and reproducing aromas not only in a computer but in all fields such as communication terminals, household products, means of transport (transportation facilities), and industrial machinery. Since a universal deployment (general-purpose) interface is provided for recording and reproducing odors, the OLP may become a standard for supporting a variety of third-party sensors and aroma reproduction apparatuses. The OLP should preferably include one or a plurality of standard bus interfaces, USB, and/or a high-speed connection interface that connects to a higher-order processor.

7. Applications

The technology and architecture relating to the generation of data including contents relating to chemical substances provided by the present invention are not limited to being applied to odors and is applicable to a variety of fields. A number out of such applications are given below, but this is not intended to limit the present invention to such applications. For example, the "electronic nose" technology provided by the OLP 100 provides a universal format and interface for generating aroma recipes and for reproducing aromas based on aroma sensing. OLP technology is capable of emulating a sense of smell for gases and chemicals using electronic technology and is capable of standardizing and integrating the protocols and/or interfaces of electronic and mechanical products to or with gases and chemicals.

Figure 15:
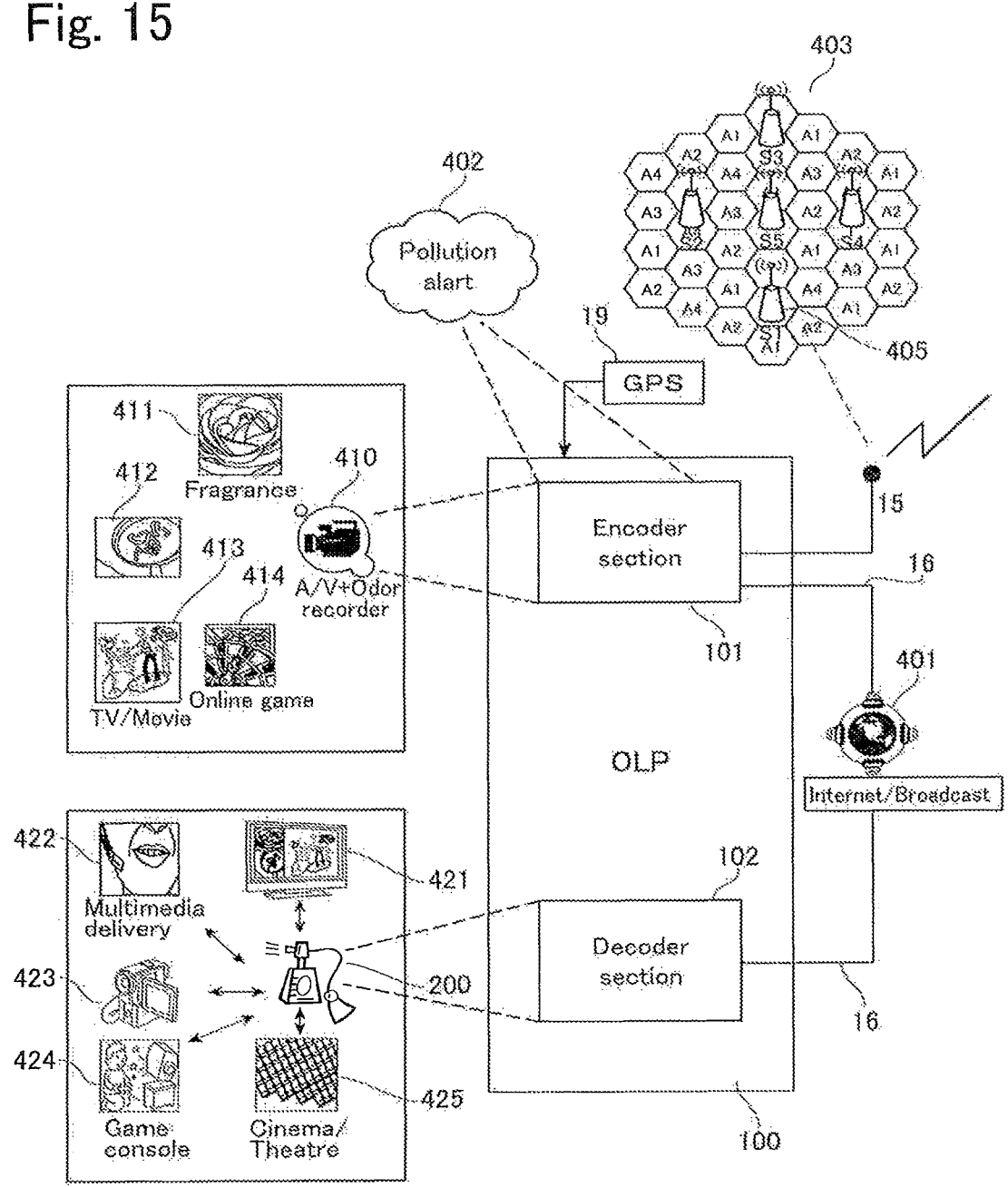
FIG. 15 is a block diagram showing one example of an application.

One typical application is an entertainment application where the OLP is linked to another multimedia appliance. As shown in FIG. 15, the encoder section 101 of the OLP 100 functions as an odor recorder 410 that is capable of recording a variety of odors 411 such as perfumes (fragrances), odors 412 relating to cooking, odors 413 relating to a screen of a television set and a movie, and odors 414 relating to a scene in a game or the like. The decoder section 102 of the OLP 100 functions as an interface of an odor reproduction apparatus 200 and is capable of having odors 421 that go together with the screen of a television set, odors 422 that go together with multimedia communication, odors 423 that go together with video, odors 424 that go together with a game, and odors 425 that go together with a movie reproduced. The encoder section 101 and the decoder section 102 are capable of connecting to a communication medium such as the Internet 401, and odor data is capable of being transmitted in real time such as Net distribution or store-and-forward-type transmission such as electronic mail.

Another typical application is stand-alone use, with a typical example of this being a monitoring application. As shown in FIG. 15, it is possible to detect a polluted region 402 using the functions of the encoder section 101 of the OLP 100. A mobile terminal or robot equipped with the OLP 100 is capable of detecting that the user has approached the polluted region 402, of informing or alerting the user and/or of investigating the pollution state of regions while patrolling the region 403. Position information obtained by the GPS 19 or position information obtained from base station information can be incorporated into the RAW data 35, and it is possible to automatically announce the areas of danger on the Web.

Figure 16:
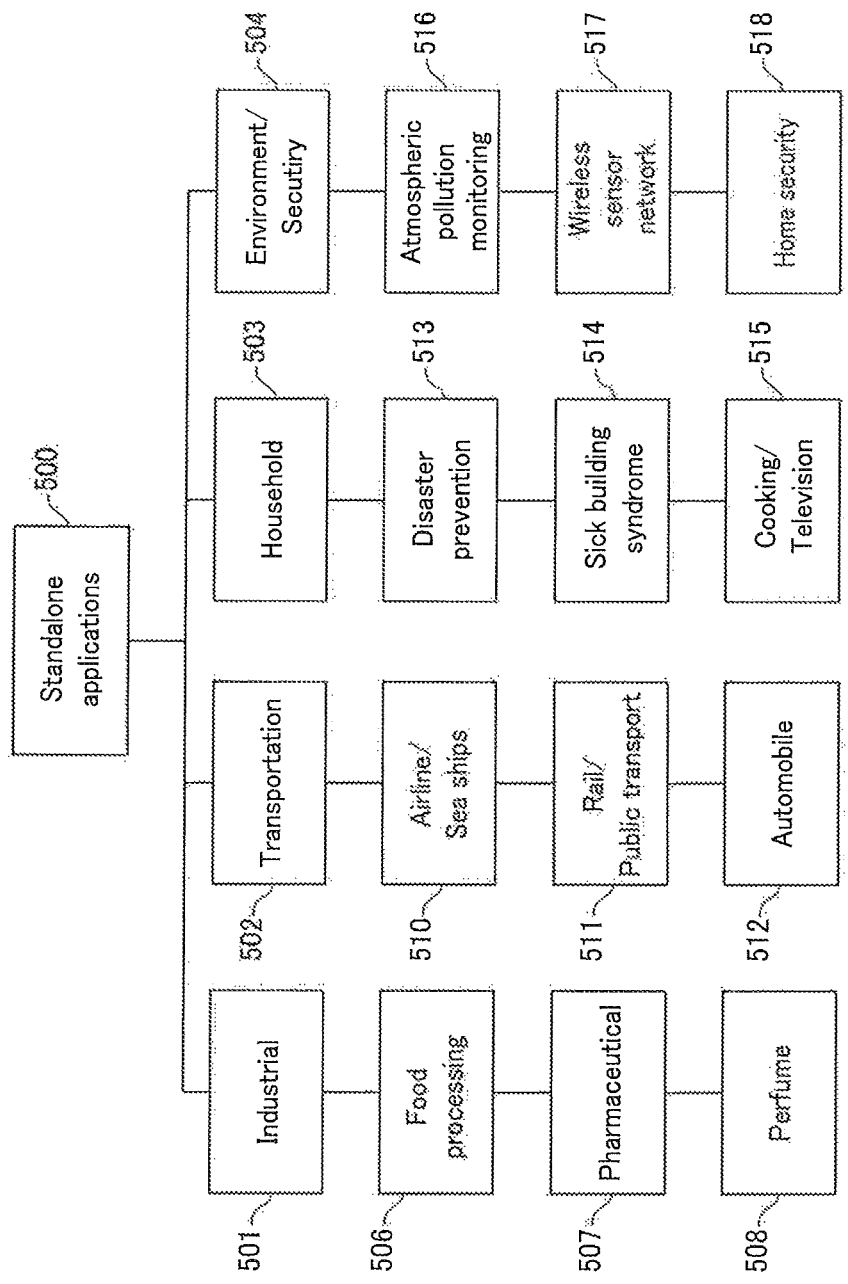
FIG. 16 is a block diagram showing a number of example applications.

FIG. 16 shows a number of applications where use of the OLP 100 in stand-alone mode is anticipated exemplary. Such applications are roughly categorized into industry 501, transportation 502, household 503, and environment/security 504. The industry field 501 includes the food sector 506, with possible examples being application to safety management, process control, poisonous substance management, and smell/odor analysis of foods, wrapping, and storage of foods. The industry field 501 also includes the pharmaceutical sector 507, with possible examples being application to drug development, medical diagnosis, and pharmacies. The industry field 501 also includes the perfume sector 508, with possible examples being application to fragrance analysis and fragrance mixing.

The transportation field 502 includes an air and/or sea transportation field 510, with possible examples being application to safety at airports and ports, customs inspections, air conditioning, multimedia services, and the like. In the rail and public transport field 511, possible applications include monitoring atmospheric pollution, indicating evacuation routes, and the like. In the automobile field 512, possible applications include safety, air conditioning, multimedia services, and the like.

The household field 503 includes disaster prevention 513, with a possible application being monitoring of carbon dioxide, oxygen, nitrogen, and ozone. In a sick building syndrome field 514, a possible application is monitoring VOCs (Volatile Organic Compounds) and formaldehyde. In a cooking/television field 515, possible applications include the addition of an odor reproduction apparatus to a domestic television set, sampling aromas of cooking, and recording the scents of food.

The environment/security field 504 includes an atmospheric pollution monitoring field 516, with a possible application being monitoring pollution at a public facility, a park, a garbage disposal plant, an industrial zone, or the like. In a wireless network sensor field 517, a possible application is monitoring ozone, temperature, humidity, pollen, and the like. In a home/home land security field 518, a possible application is monitoring the safety and health of citizens.

Figure 17:
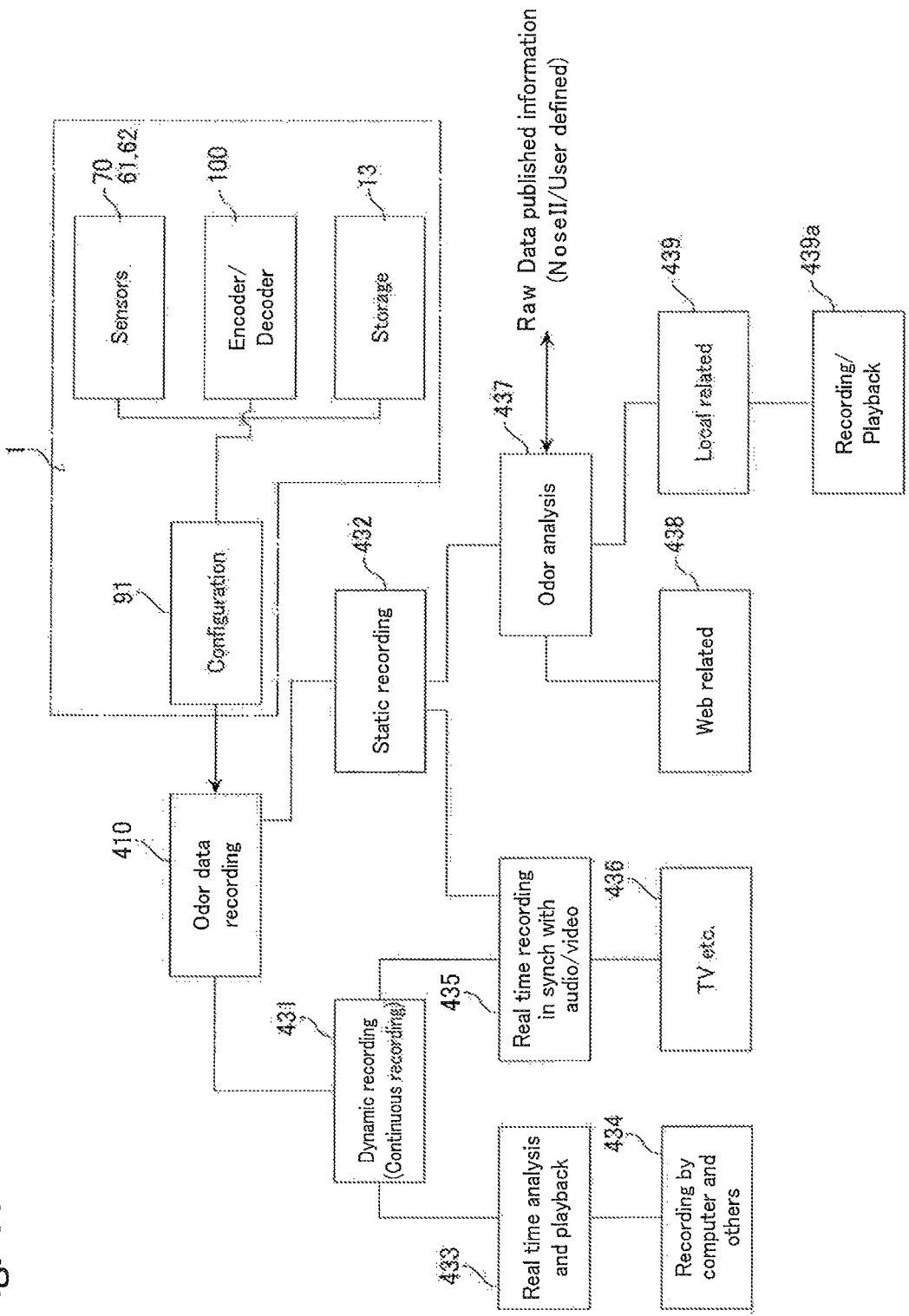
FIG. 17 is a flowchart showing applications that record and reproduces odors.

FIG. 17 is a flowchart that shows applications of recoding of odors, where a configuration 91 of recording odors is applied or set in the system 1. Odor data recording 410 includes dynamic recording (continuous recording) 431 and static recording (snapshots) 432. Both types of recording includes items that are automatically managed by machine or the use. For the snapshots 432, a period such as two seconds, five seconds, and ten seconds can be designated by the user. For dynamic recording 431, real-time analysis and playback (reproduction) 433 are possible, with computer recording 434 also being possible. Possible applications include advertising, online chat, games, cooking programs, and the like. Real time recording 435 that is synchronized with audio (sound) and/or video (images) is also possible, with odor-enhanced broadcasts and use in advertising being possible for television 436.

For static recording 432, odor analysis 437 may be the main application. Web-related applications 438 could include application to services such as online pattern searching, a telephone olfaction service, diagnosis, odor comparison, the downloading of mixing recipes for perfume, and the like. Local-related applications 439 could include application to machine learning, analysis, messaging, information sharing, three-dimensional view, odor display and the like. In addition, local recording and playback are also possible (439*a*).

Figure 18:
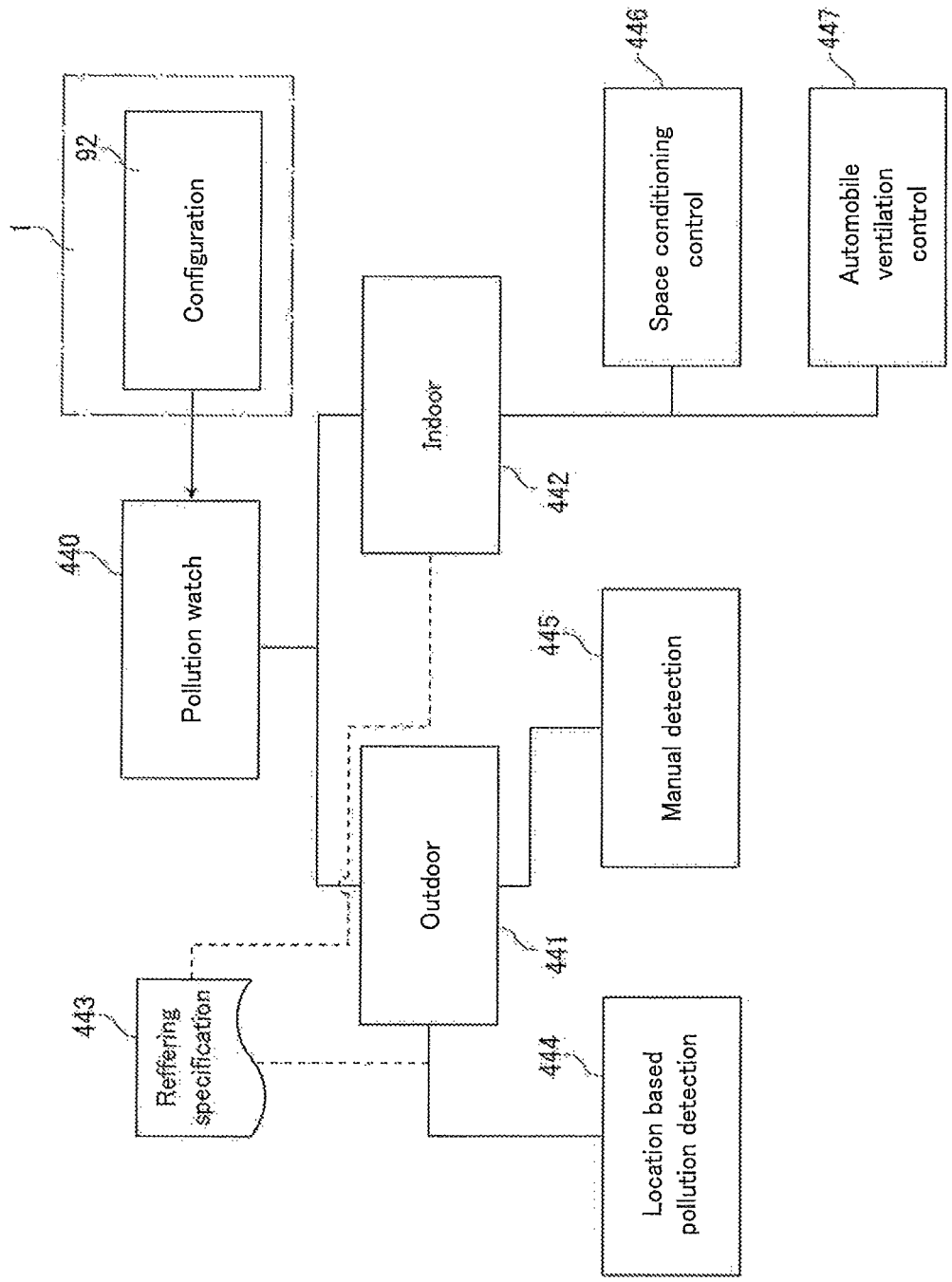
FIG. 18 is a flowchart showing applications for pollution monitoring.

FIG. 18 is a flowchart that shows applications of monitoring pollution, where a configuration 92 of monitoring pollution is applied or set in the system 1. Pollution watch (monitoring) 440 includes outdoor 441 and indoor 442 applications. In both cases, monitoring is carried out by referring to pollution standard information 443 set by the national government or the like. Outdoor 441 includes a location-based pollution detection application 444. Here, it is effective to combine the OLP 100 and a handheld device (mobile telephone, laptop computer, wireless Internet device), with it being possible to obtain and display pollution information based on position information. Application to manual detection 445 is also possible, and includes detection of pollutants and VOCs. For indoor 442, application to control 446 of air conditioning equipment is possible. Other possible applications are monitoring indoor air state, ventilation control of air conditioners, and gas leak alarms. Another possible application is air conditioning control 447 in an automobile. Monitoring air quality, monitoring combustion, and supplying multimedia and aromas are also possible.

FIG. 19 is a flowchart that shows applications of health monitoring, where a configuration 93 of monitoring health is applied or set in the system 1. Health monitoring 450 includes breath analysis 451 and diagnosis/prevention 452. Breath analysis 451 here includes analysis 453 of body odor/mouth odor and alcohol level detection (breathalyzing) 454. Diagnosis/prevention 452 includes allergy measures 456, with possible applications including detection of allergens, gases that act as stimuli, asthma triggers, pollen, and the like. Application to detection of carcinogens and detection of harmful chemicals 457 is also possible. Another possible application is metabolic syndrome measures 458.

In this way, the OLP 100 realizes a variety of processes based on user programs, and interacts with the user via a variety of applications/interfaces to capture, record/reproduce, monitor, and analyze an aroma or gas, and the OLP 100 supplies functions as an electronic nose. In a security context, a system equipped with an OLP outputs warning to the users on the direction and/or near the position of a source of danger so that the users can move away from the source. As an example, a sensor is mounted on a base so as to revolve by an appropriate angle. On the other hand, a system equipped with the OLP is also capable of being used to capture an aroma, detect the direction and distance to the aroma source, and guide the user thereto.

By obtaining an aroma signature and a fingerprint of a chemical constituent from a database, it is possible to provide respectively different actions for various odors. The database may be stored in a local memory. User can train the local database to learn new odors and the characteristics. On the other hand, it is also possible to provide services that manage unauthorized (nonpublic) odor data using the Web or an online database.

Displaying animation should be one of examples of output of detailed information relating to aroma characteristics. It is possible to visually represent the aroma. In one possible application, an aroma reproduction unit uses animation for displaying compounds and characteristics thereof using a 3D display.

Interfaces for applications and/or users are an important aspect of the OLP. There are a number of methods for expressing an olfactory action or aroma content. One natural method may reproduce the aromas themselves using an aroma reproduction apparatus as an olfactory display or a haptic display.

The invention claimed is:

1. A system for generating first data including content data related to a chemical substance in a test gas, wherein the chemical substance includes at least one of a compound, a molecule, and an element, the system comprises:
a mass spectrometer sensor, the mass spectrometer sensor is configured such that the sensitivity, resolution or selectivity of the mass spectrometer sensor is controlled according to setting conditions;
an interface for outputting the content data, including an intensity change indicative of a detected chemical substance contained in data from the mass spectrometer sensor; and
a mass spectrometer sensor controller that is configured to:
carry out an analysis of the data from the mass spectrometer sensor, wherein the mass spectrometer sensor controller is configured to carry out a preliminary analysis with initial setting conditions designed for scanning in a first range using a test sample prepared in advance, the test sample and initial setting conditions being selected according to an application configured to capture, record, monitor or analyze gases in the test gas, and the setting conditions include at least one of a voltage for ionizing, a voltage for scanning a spectrum region, and a scanning speed for detecting a chemical substance,
change the setting conditions for the mass spectrometer sensor according to content data generated during the preliminary analysis of the test sample to improve sensitivity and selectivity, and
carry out a test scan using the changed setting conditions for the chemical substance in the test gas wherein the test scan for the chemical substance is carried out after the settings of the mass spectrometer sensor have been compensated with consideration to a temperature of the test gas to correct for drifting of the sensor data caused by changes in the temperature of the test gas.

2. The system according to claim 1, wherein the first range of the preliminary analysis is wider than a range carried out by the changed setting condition.

3. A method for controlling a system for generating first data including content data related to a chemical substance in a test gas, wherein the chemical substance includes at least one of a compound, a molecule, and an element, wherein the system comprises:
a mass spectrometer sensor, the mass spectrometer sensor is configured such that the sensitivity, resolution or selectivity of the mass spectrometer sensor is controlled according to setting conditions;
an interface for outputting the content data including an intensity change indicative of a detected chemical substance contained in data from the mass spectrometer sensor,
and the method comprises:
carrying out a preliminary analysis of the data from the mass spectrometer sensor, wherein the mass spectrometer sensor controller carries out a preliminary analysis with initial setting conditions designed for scanning in a first range using a test sample prepared in advance, the test sample and initial setting conditions being selected according to an application configured to capture, record, monitor or analyze gases in the test gas, and the setting conditions include at least one of a voltage for ionizing, a voltage for scanning a spectrum region, and a scanning speed for detecting a chemical substance,
changing the setting conditions for the mass spectrometer sensor according to content data generated during the preliminary analysis of the test sample to improve sensitivity and selectivity, and
carrying out a test scan using the changed setting conditions for the chemical substance in the test gas wherein the test scan for the chemical substance is carried out after the settings of the mass spectrometer sensor have been compensated with consideration to a temperature of the test gas to correct for drifting of the sensor data caused by changes in the temperature of the test gas.

4. The method according to claim 3, wherein the first range of the preliminary analysis is wider than a range carried out by the changed setting condition.

\* \* \* \* \*